(12) United States Patent
Ben-Zion et al.

(10) Patent No.: US 11,034,697 B2
(45) Date of Patent: Jun. 15, 2021

(54) PROCESS FOR THE PREPARATION OF REMIMAZOLAM AND SOLID STATE FORMS OF REMIMAZOLAM SALTS

(71) Applicant: WATSON LABORATORIES INC., Corona, CA (US)

(72) Inventors: Dolitzky Ben-Zion, Petach Tikva (IL); Mendelovici Marioara, Rehovot (IL); Bodkhe Arjun Rajaram, Thane (IN); Mane Ganesh Shivaji, Thane (IN); Samala Rajamouli Srihari, Thane (IN); Joshi Ashutosh Vijay, Thane (IN); Parven Kumar Luthra, New Delhi (IN); Amit Singh, Greater Noida (IN); Anantha Rajmohan Muthusamy, Delhi (IN)

(73) Assignee: WATSON LABORATORIES INC., Corona, CA (US)

( * ) Notice: Subject to any disclaimer, the term of this patent is extended or adjusted under 35 U.S.C. 154(b) by 0 days.

(21) Appl. No.: 16/484,165

(22) PCT Filed: Feb. 8, 2018

(86) PCT No.: PCT/US2018/017347
§ 371 (c)(1),
(2) Date: Aug. 7, 2019

(87) PCT Pub. No.: WO2018/148361
PCT Pub. Date: Aug. 16, 2018

(65) Prior Publication Data
US 2019/0359619 A1    Nov. 28, 2019

(30) Foreign Application Priority Data

Feb. 9, 2017 (IN) .............................. 201711004706
Sep. 20, 2017 (IN) .............................. 201711033273
Dec. 27, 2017 (IN) .............................. 201711046934
Jan. 18, 2018 (IN) .............................. 201811002128

(51) Int. Cl.
*C07D 487/04* (2006.01)
*A61P 23/00* (2006.01)
*C07D 405/14* (2006.01)

(52) U.S. Cl.
CPC ............ *C07D 487/04* (2013.01); *A61P 23/00* (2018.01); *C07D 405/14* (2013.01); *C07B 2200/13* (2013.01)

(58) Field of Classification Search
CPC ..................................................... C07D 487/04
USPC .......................................................... 514/220
See application file for complete search history.

(56) References Cited

U.S. PATENT DOCUMENTS

| 7,485,635 | B2 | 2/2009 | Feldman et al. |
| 9,156,842 | B2 | 10/2015 | Tilbrook et al. |
| 2016/0009680 | A1 | 1/2016 | Kawakami et al. |

FOREIGN PATENT DOCUMENTS

WO    2019072944 A1    4/2019

OTHER PUBLICATIONS

International Search Report and Written Opinion issued in corresponding Appl. No. PCT/US2018/017347 dated Jun. 19, 2018 (17 pages).
European communication pursuant to Article 94(3) issued in corresponding Application No. EP 18706147.8 dated Jan. 19, 2021 (4 pages).

*Primary Examiner* — Kahsay Habte
(74) *Attorney, Agent, or Firm* — Carter, DeLuca & Farrell LLP

(57) ABSTRACT

The present disclosure relates to novel processes for the preparation of short acting benzodiazepines as well as to novel intermediates in this process. More particularly the disclosure relates to processes and intermediates for preparation of Methyl 3-[(4S)-8-bromo-1-methyl-6-(pyridin-2-yl)-4H-imidazo[1,2-a][1,4]benzodiazepin-4-yl]propanoate, commonly known as Remimazolam. The present disclosure also relates to solid state forms of Remimazolam salts, processes for the preparation thereof, pharmaceutical formulations/compositions thereof, and methods of use thereof.

20 Claims, 19 Drawing Sheets

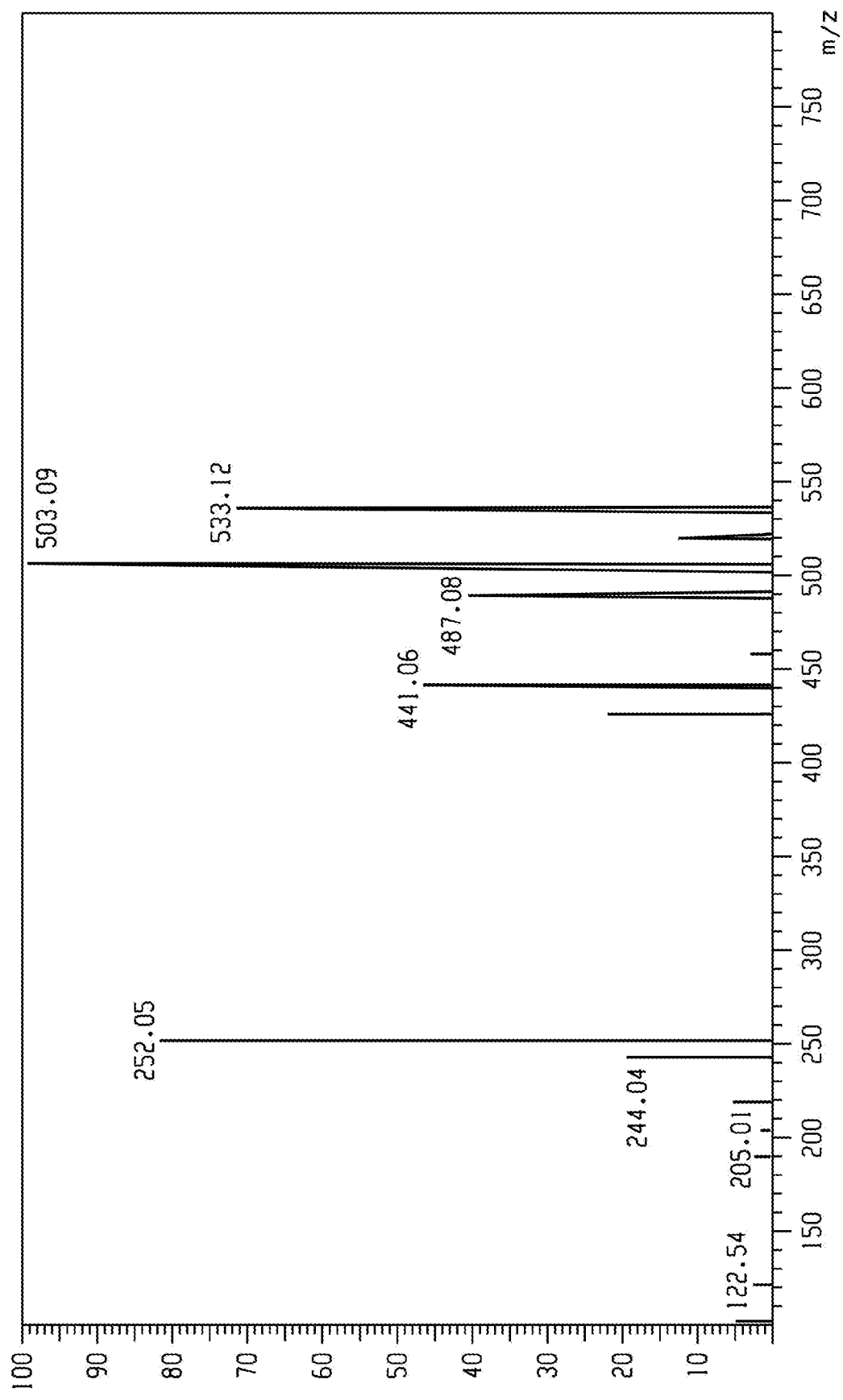
Figure 1: Mass Spectra of the compound of Formula III-S:

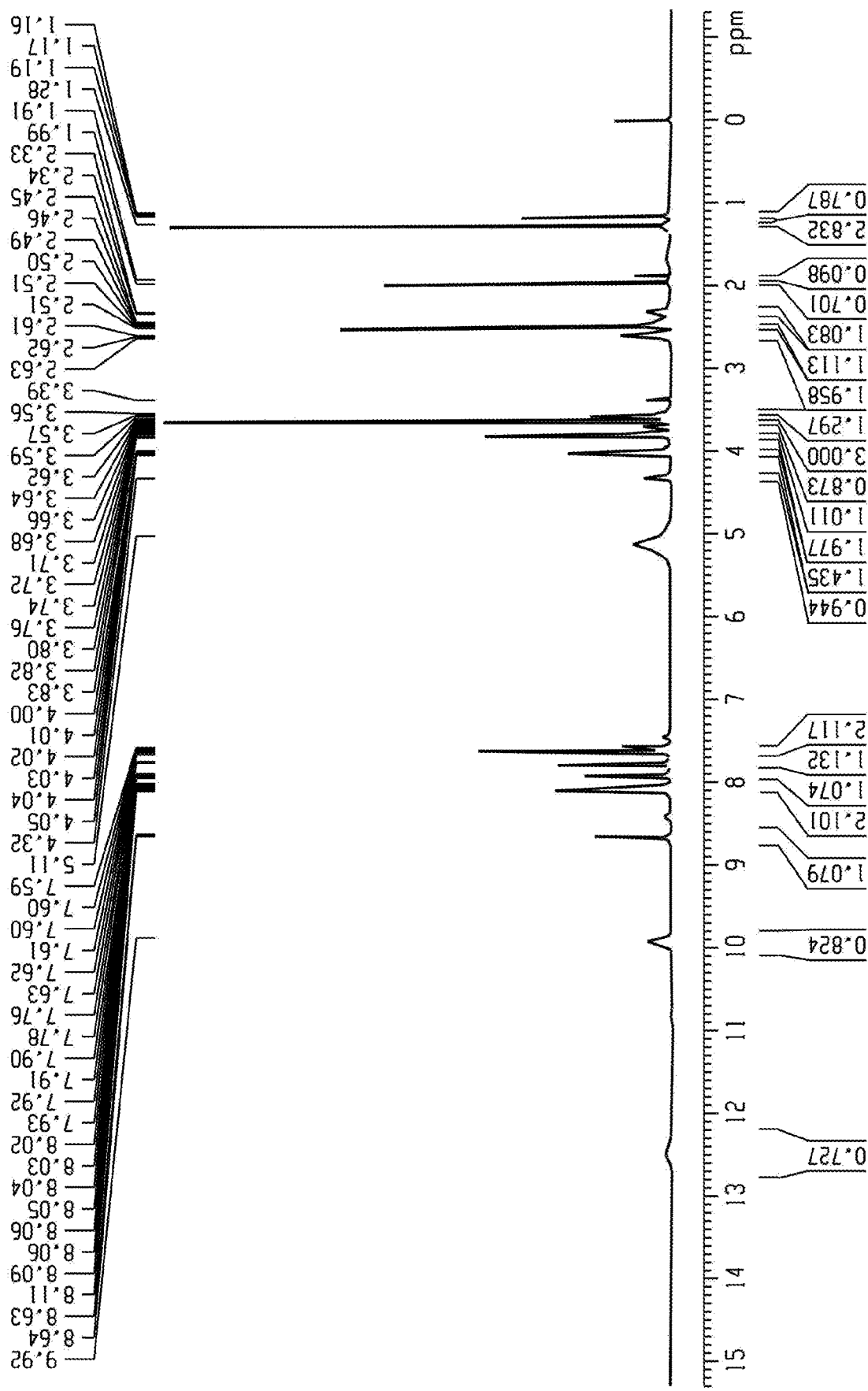

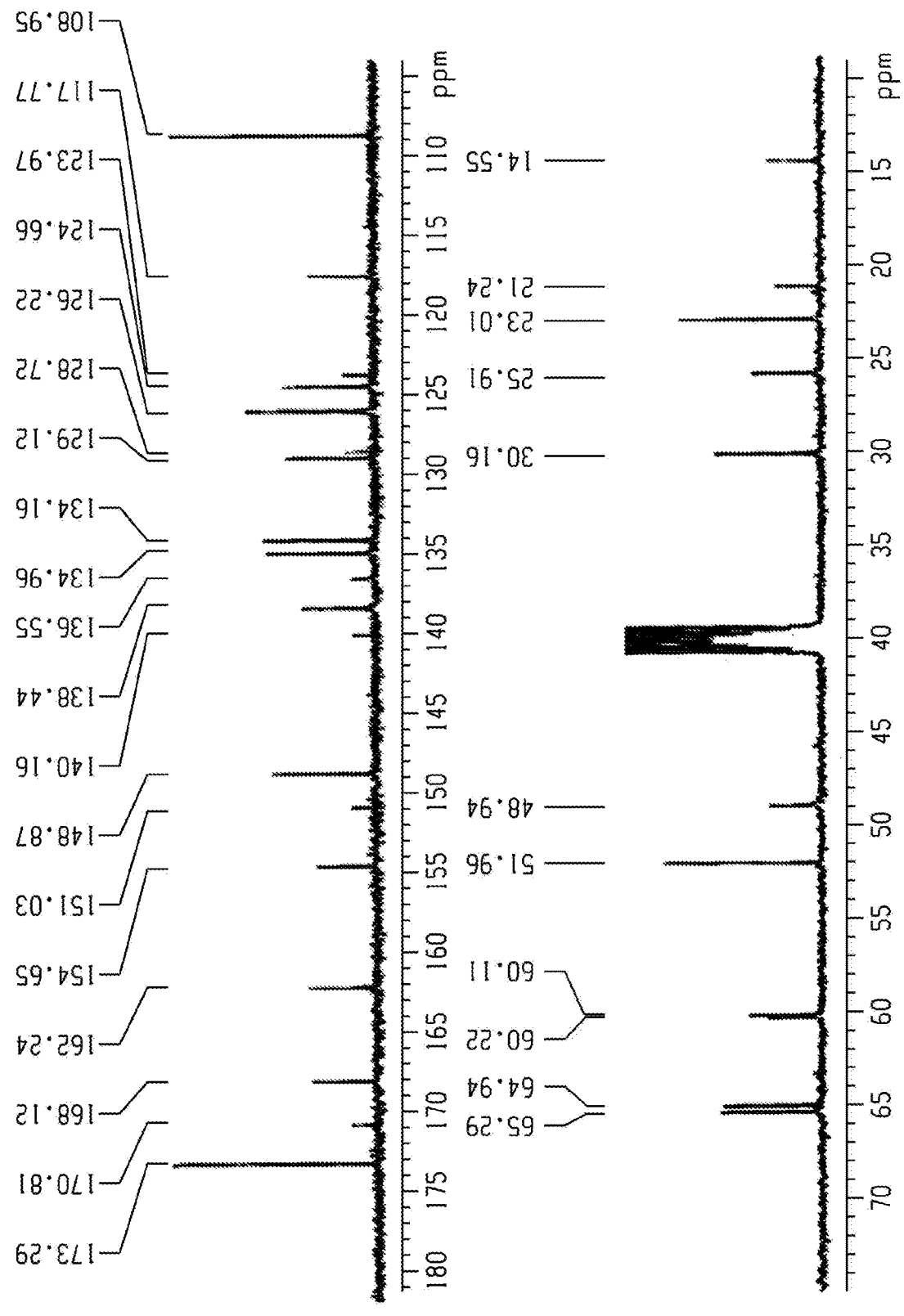
Figure 3: 13C-NMR Spectra of the compound of Formula III-S:

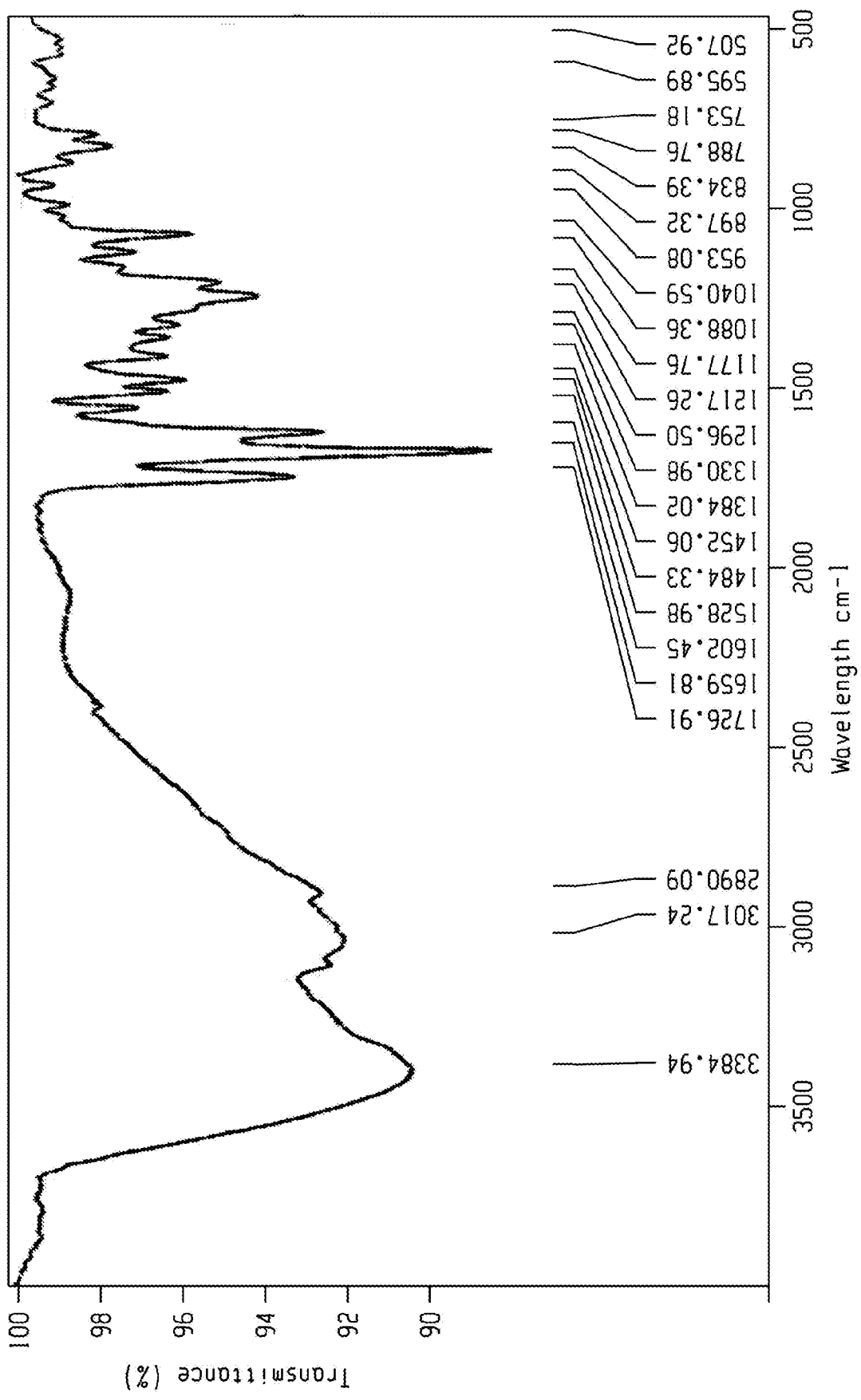
Figure 4: IR Spectra of the compound of Formula III-S

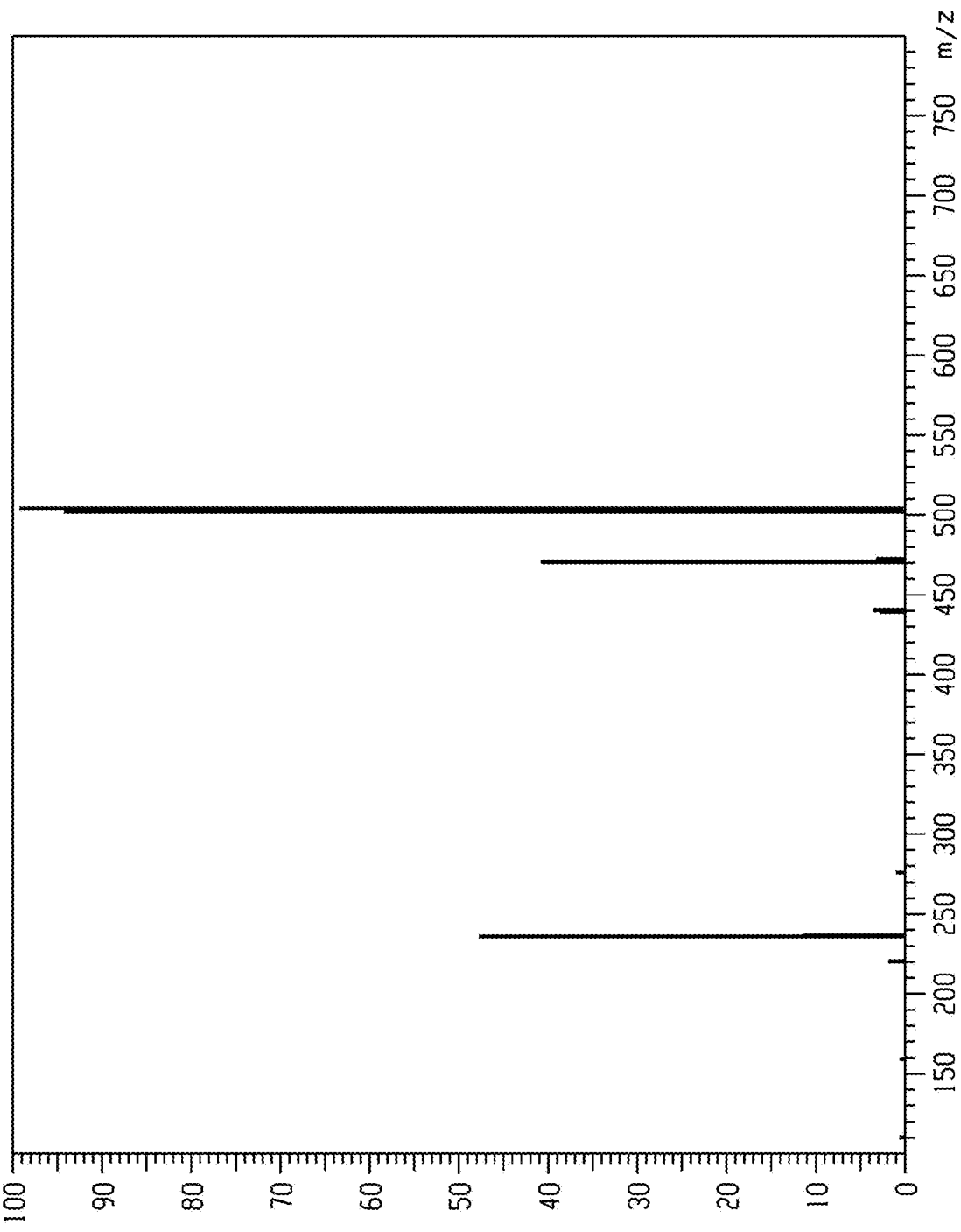

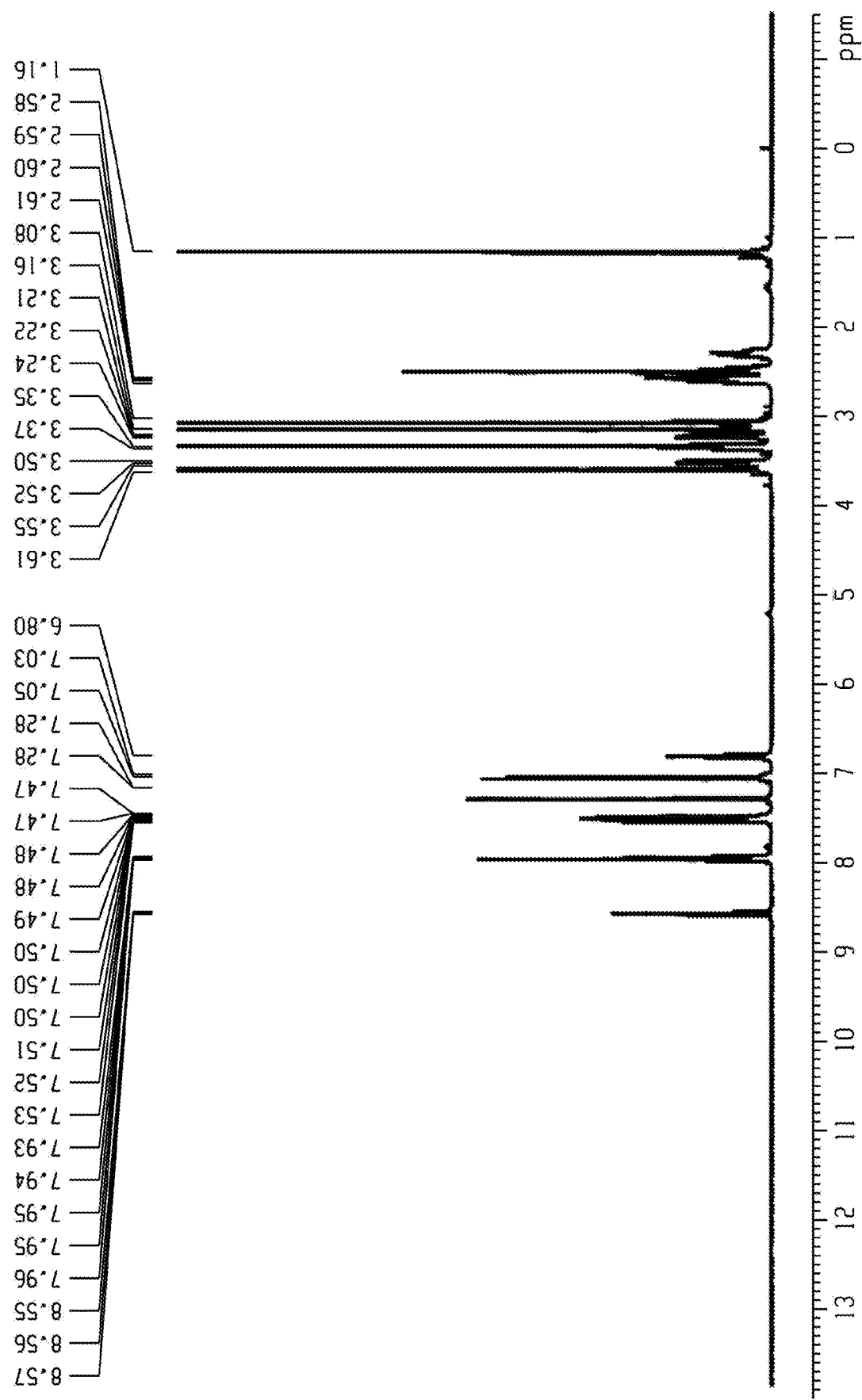
Figure 6: ¹H-NMR Spectra of formula III-13S

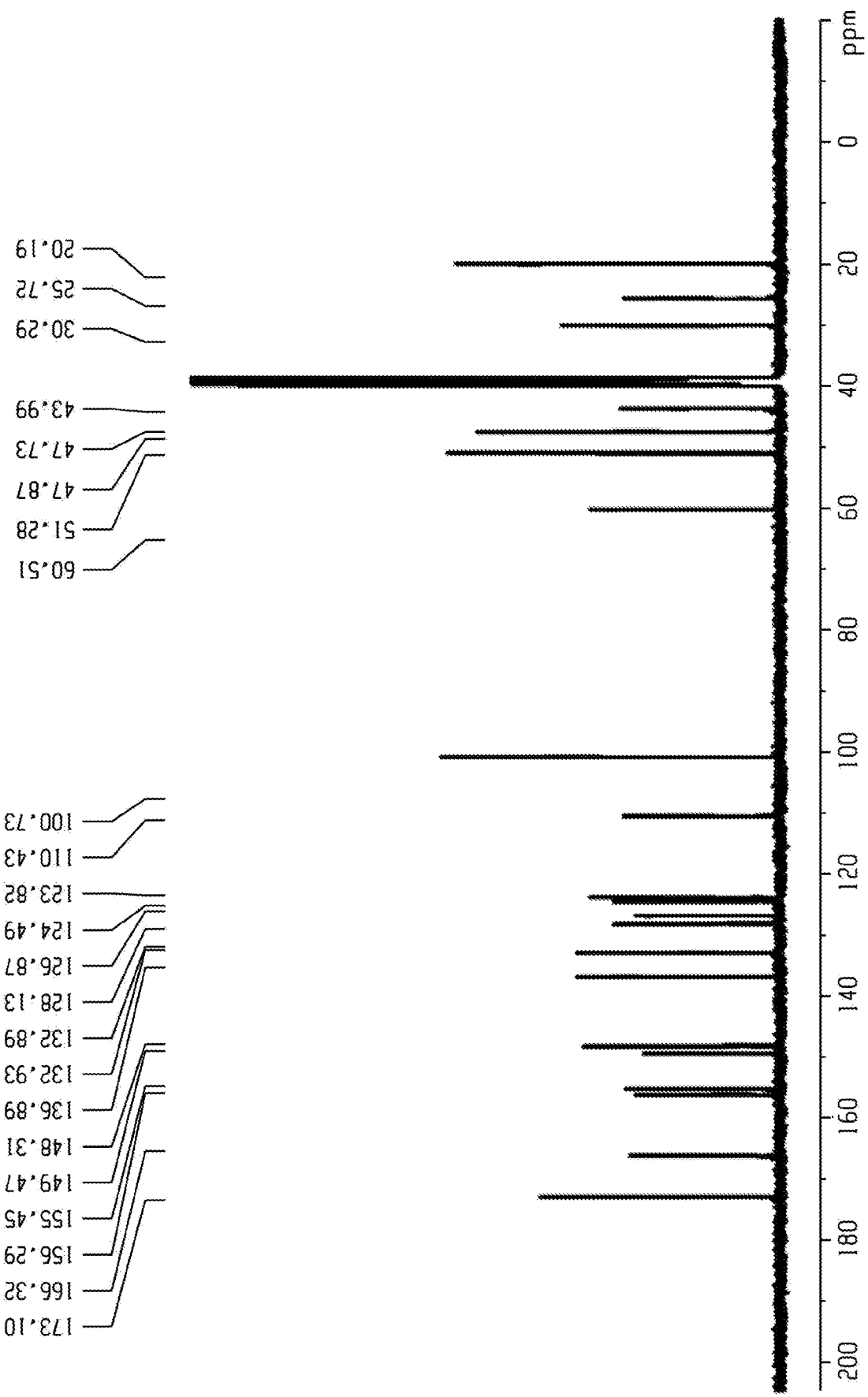
Figure 7: 13C-NMR Spectra of formula III-13S

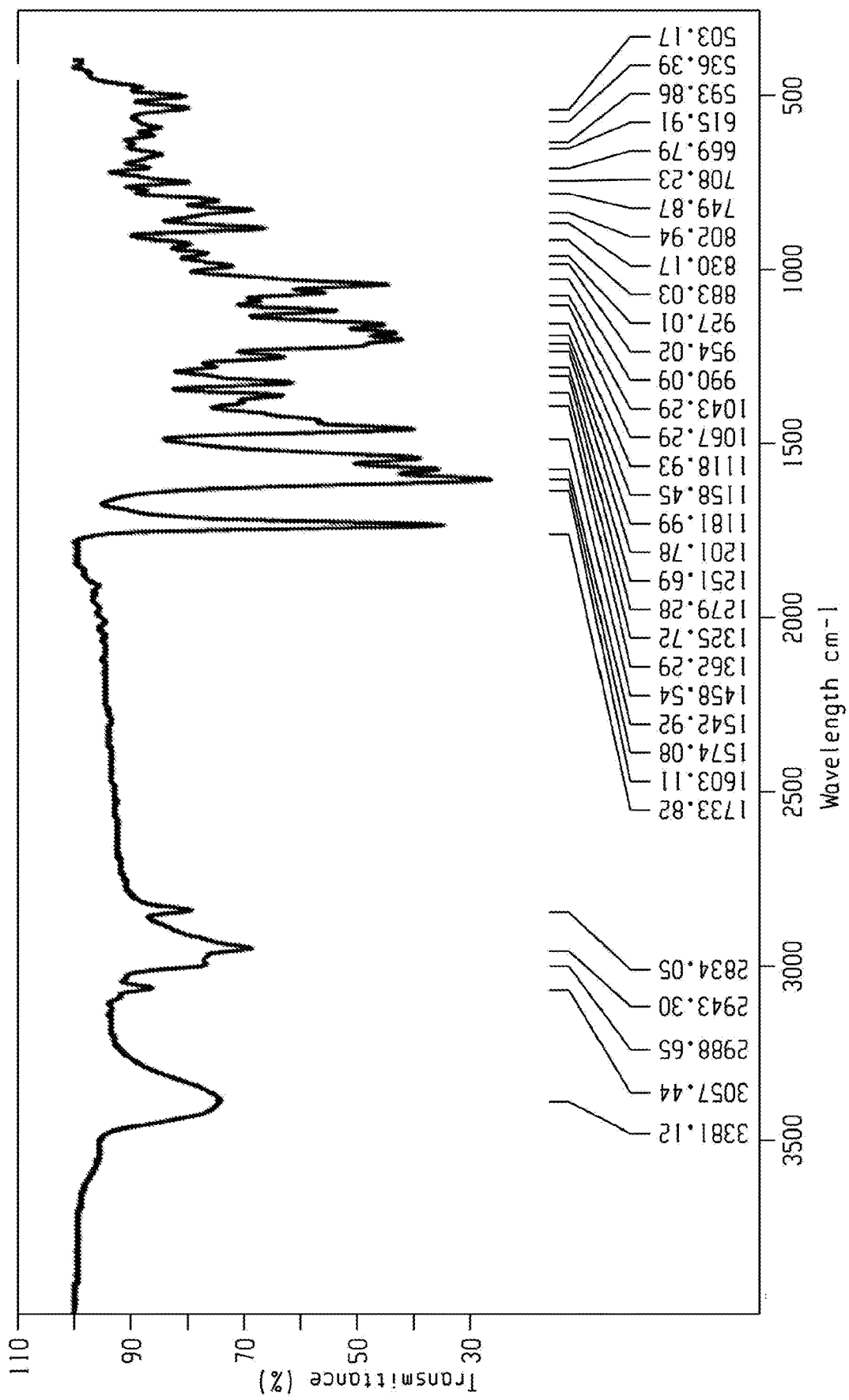
Figure 8: IR Spectra of formula III-13S

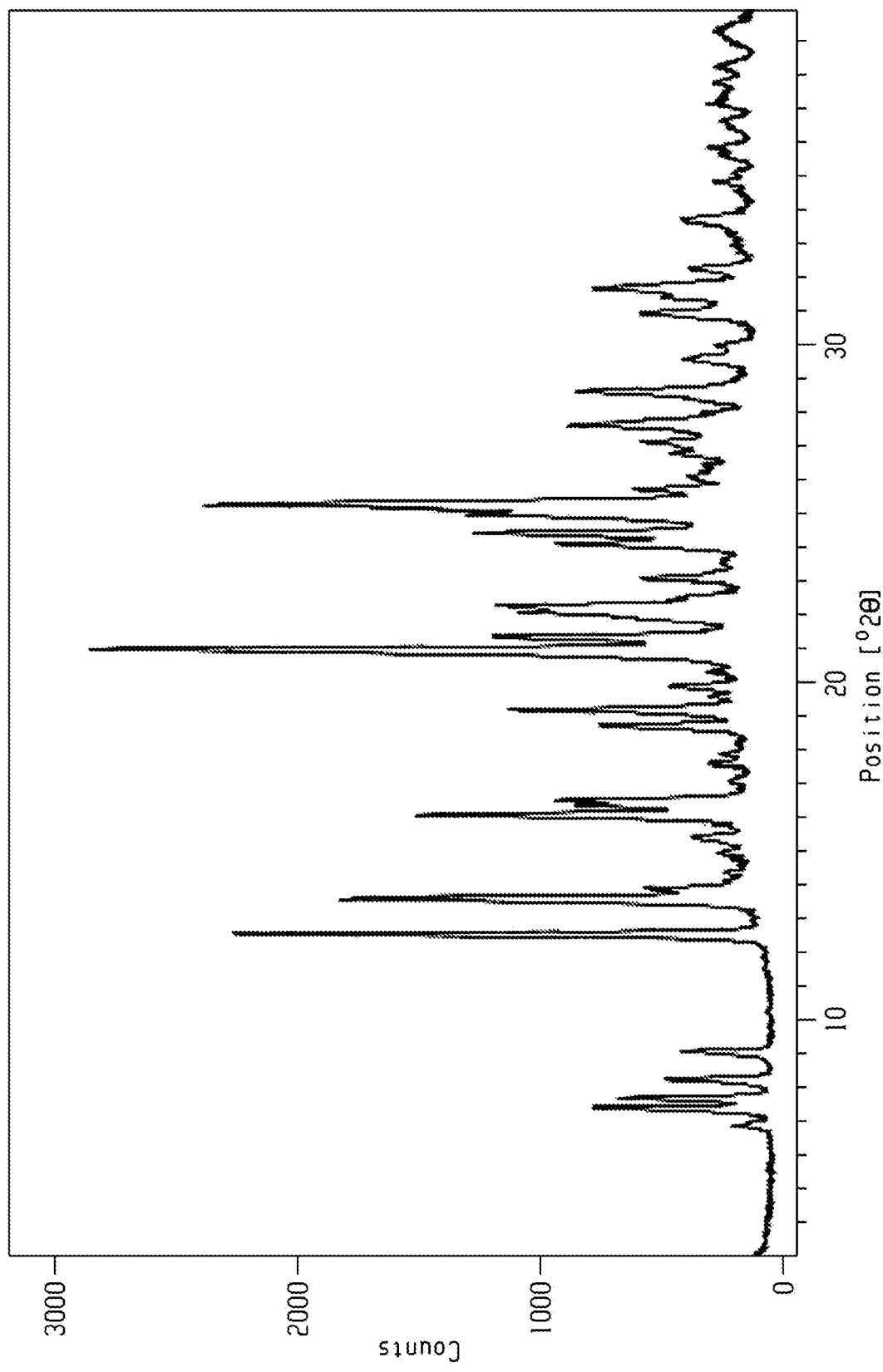

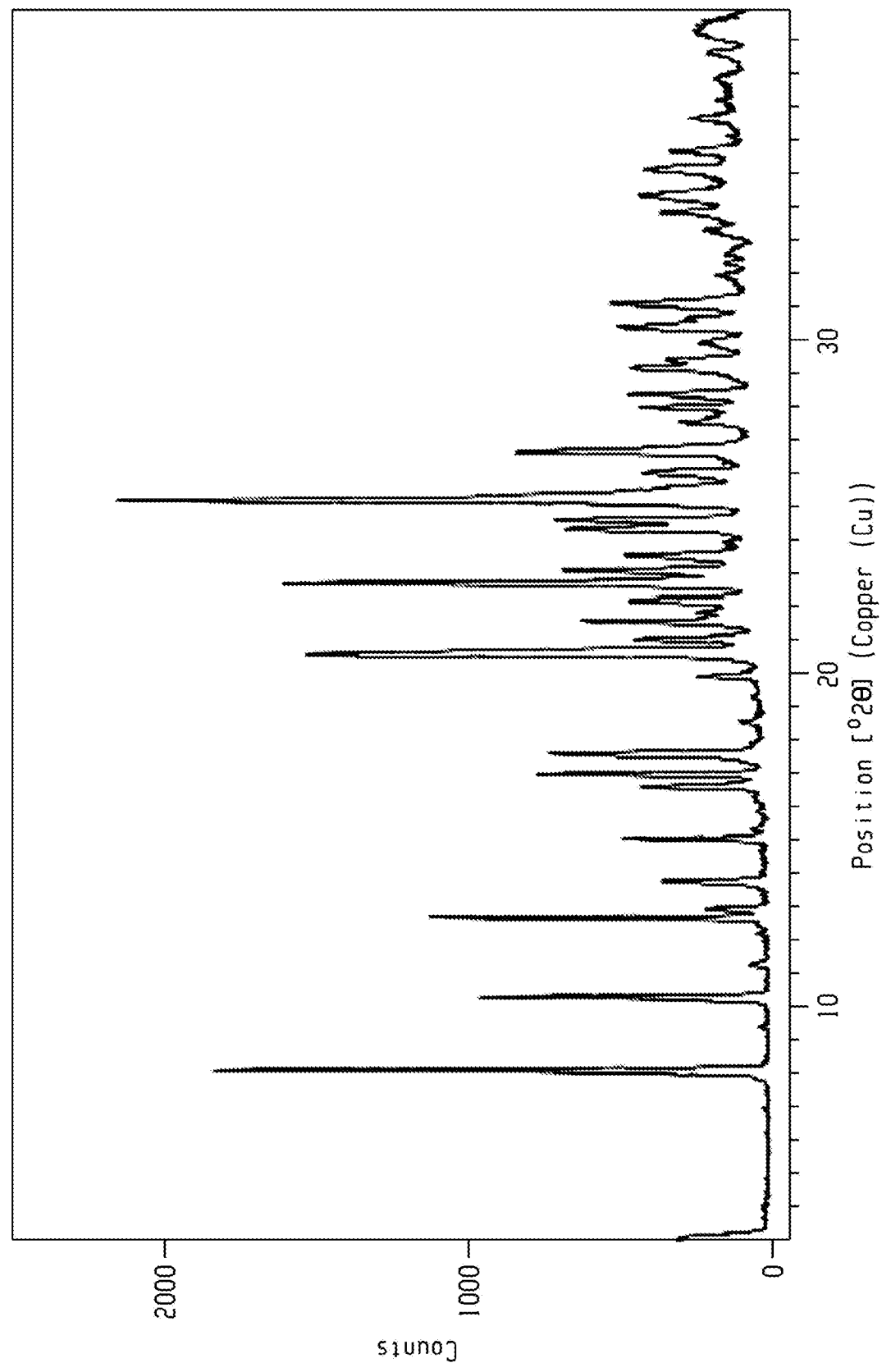

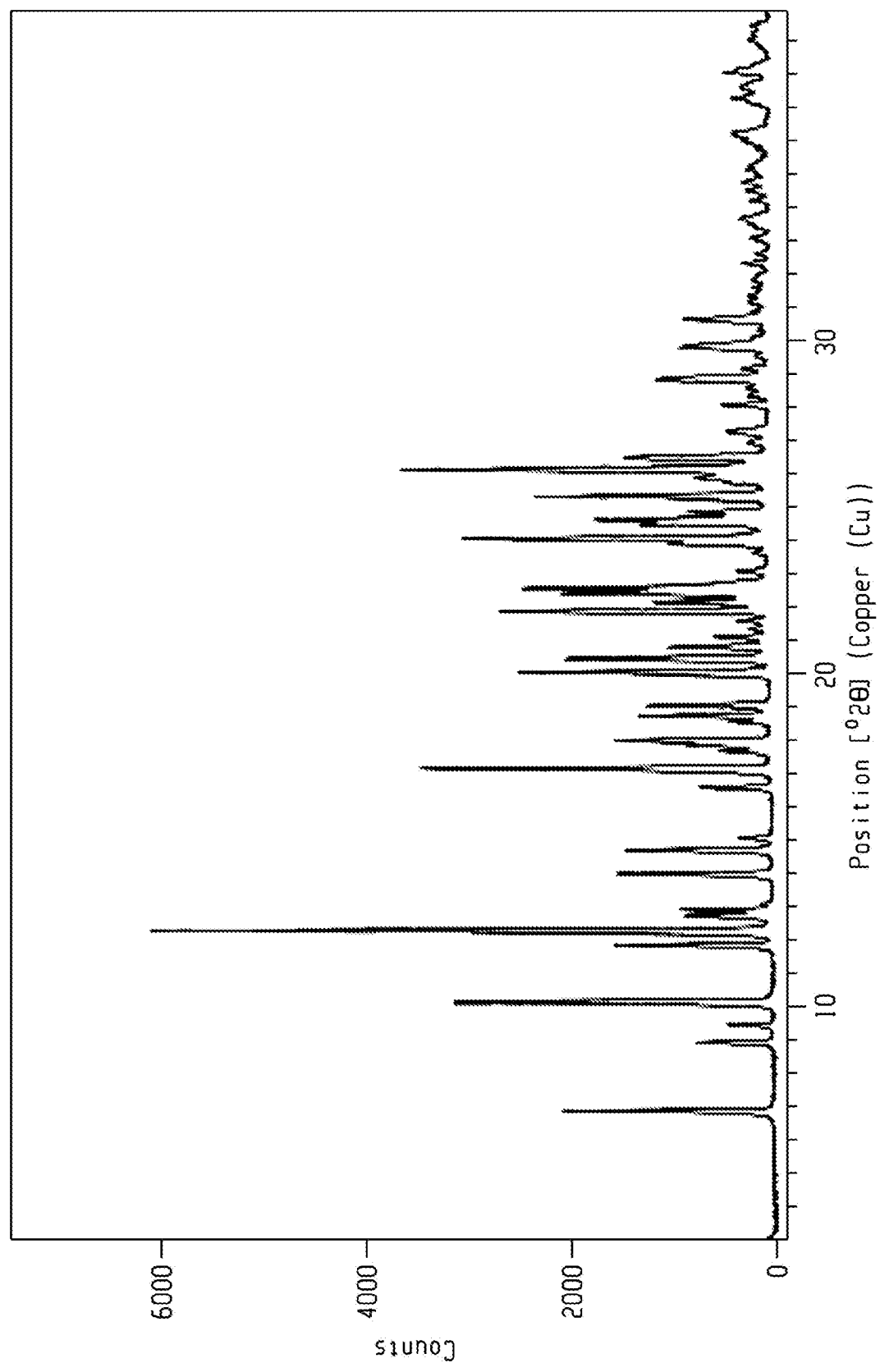

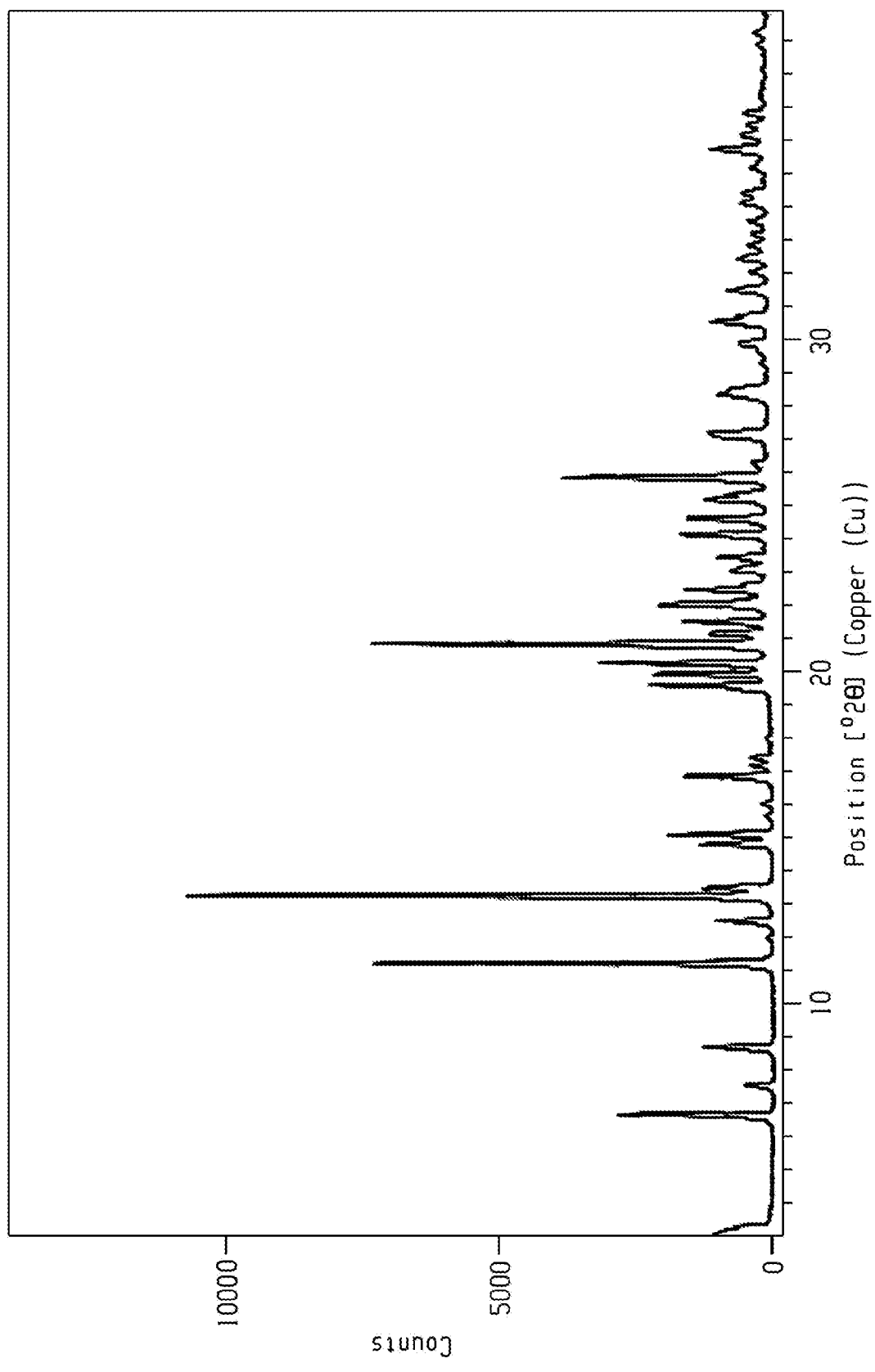
Figure 12: Remimazolam Oxalate Form 1

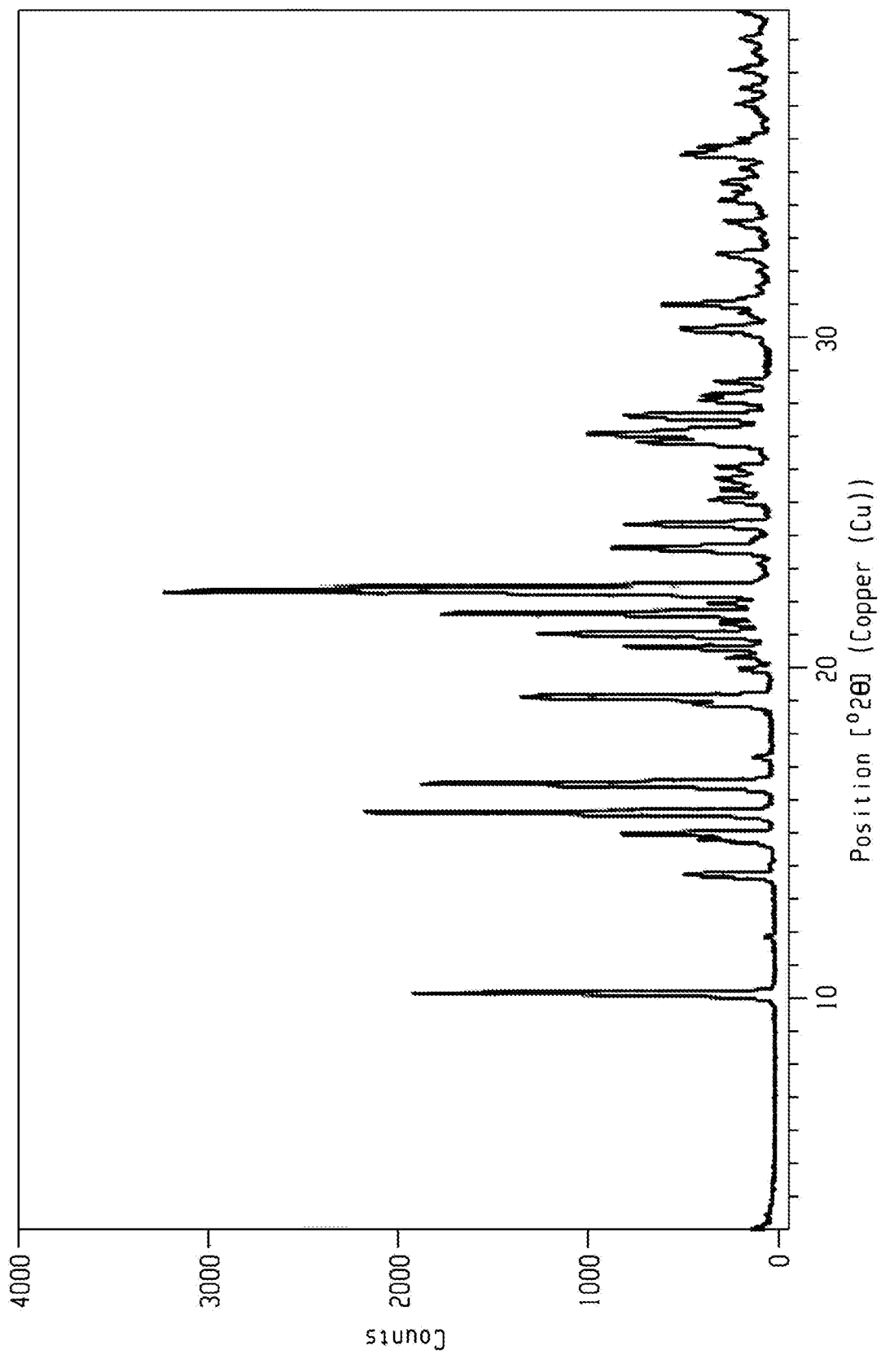

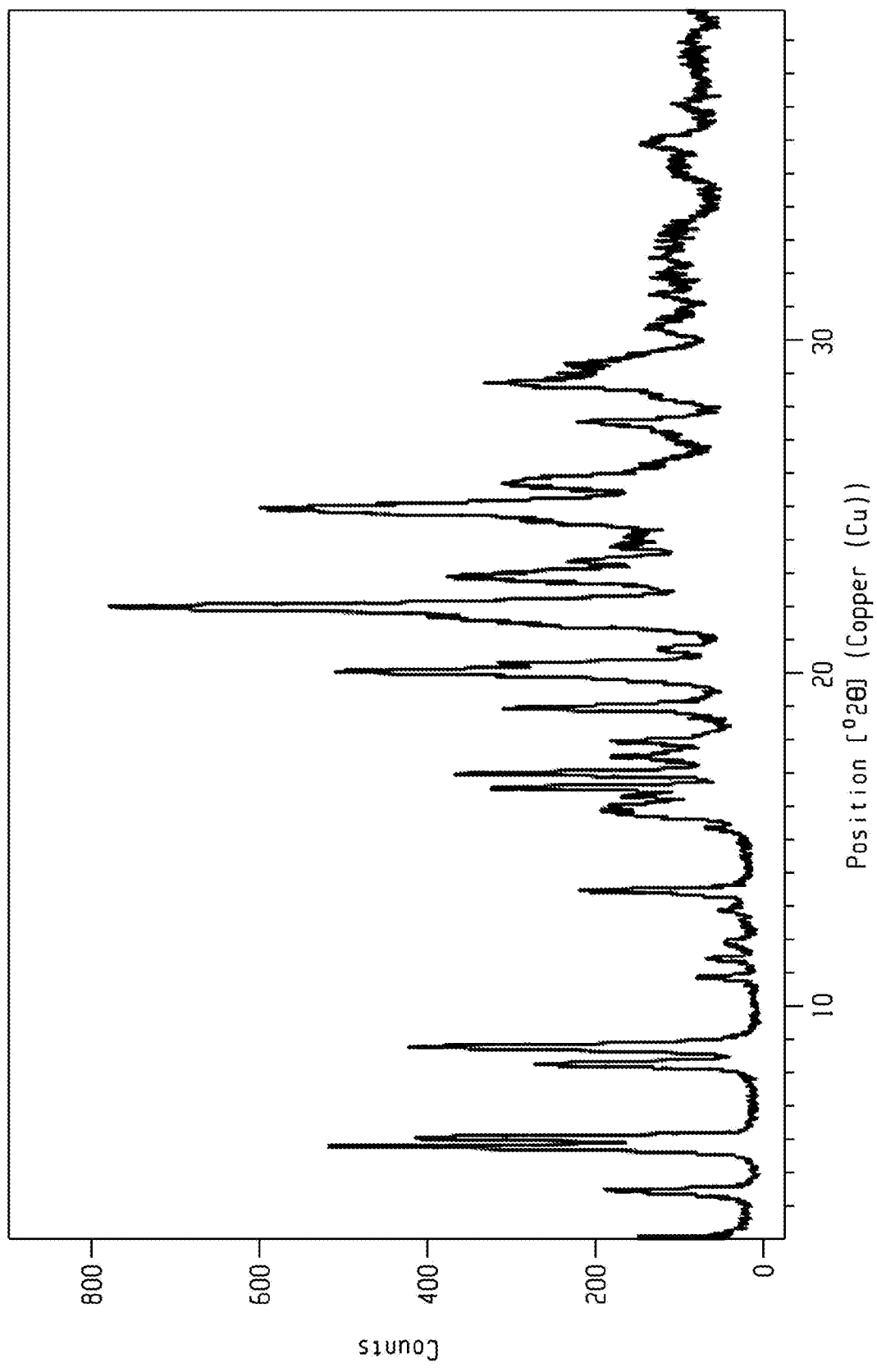
Figure 14: Remimazolam Methane Sulfonate Form 1

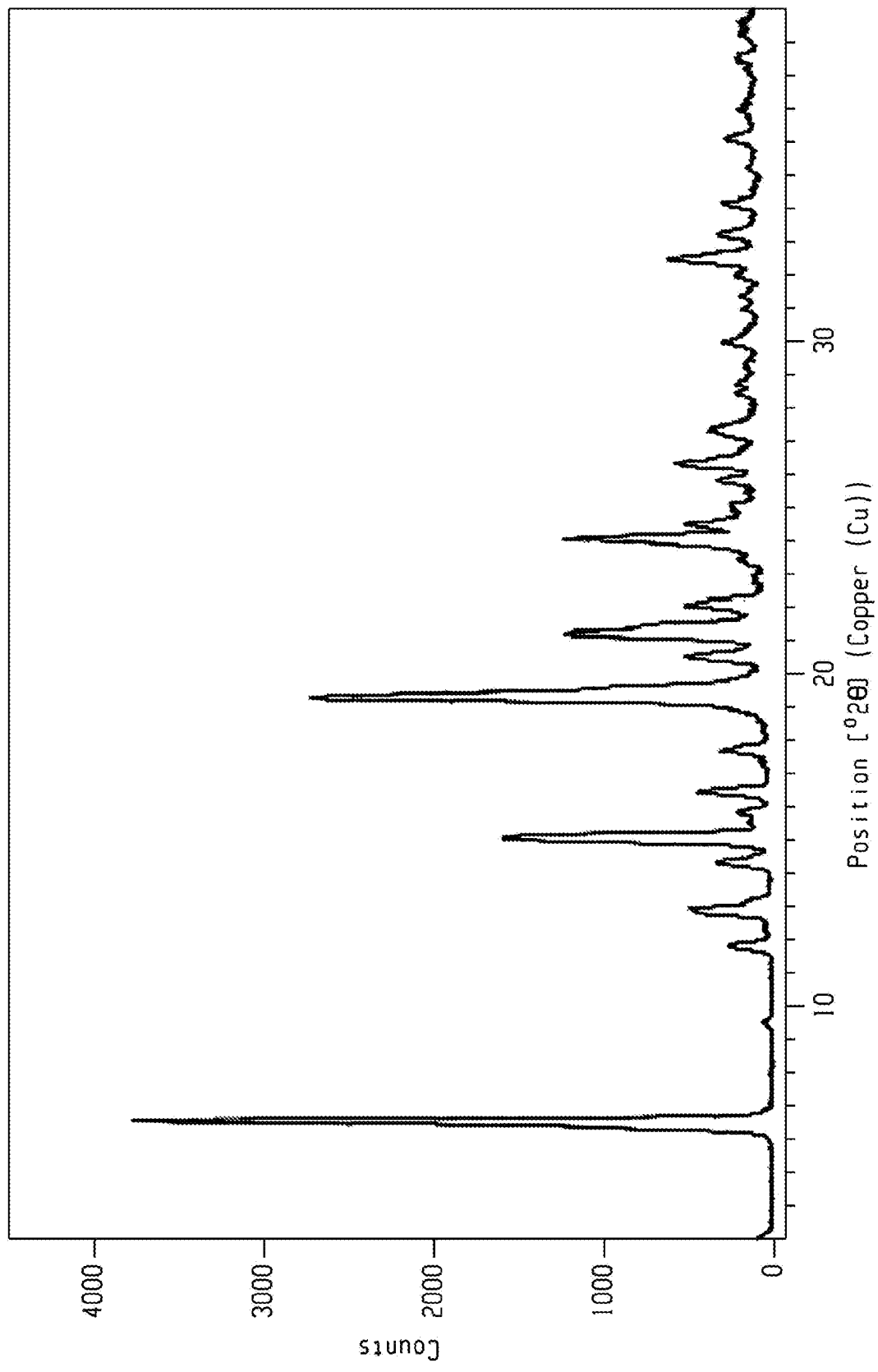

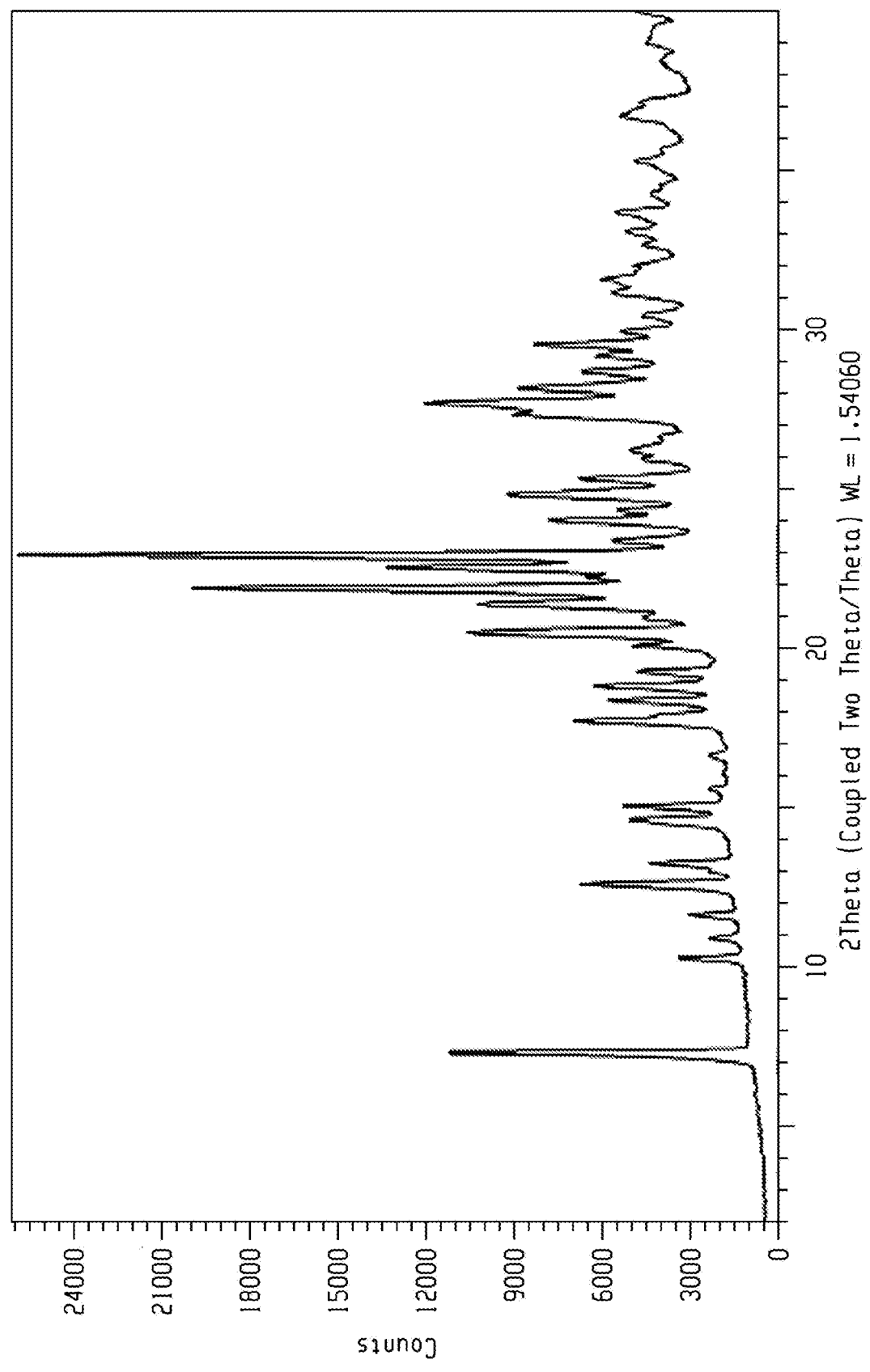

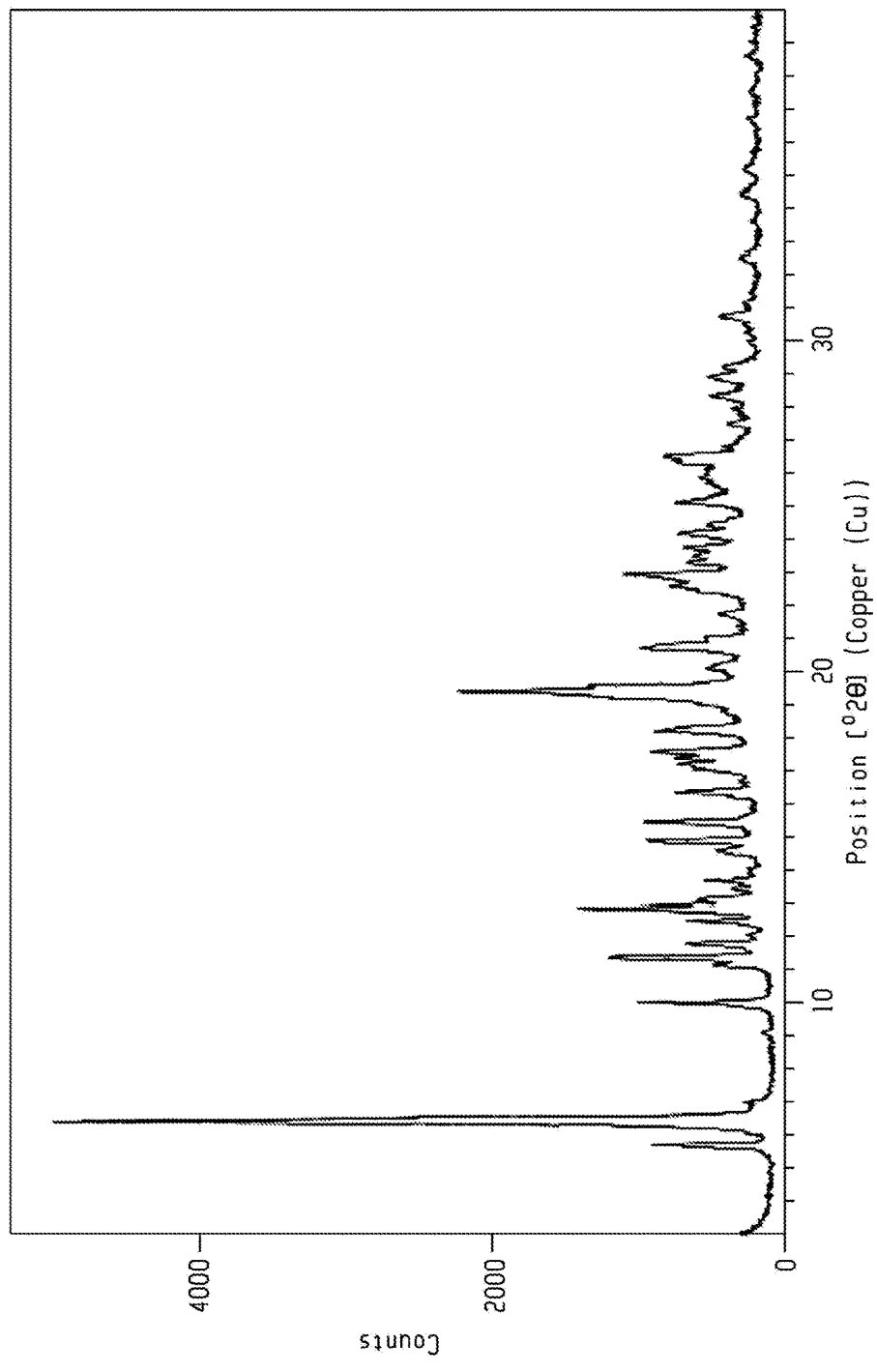

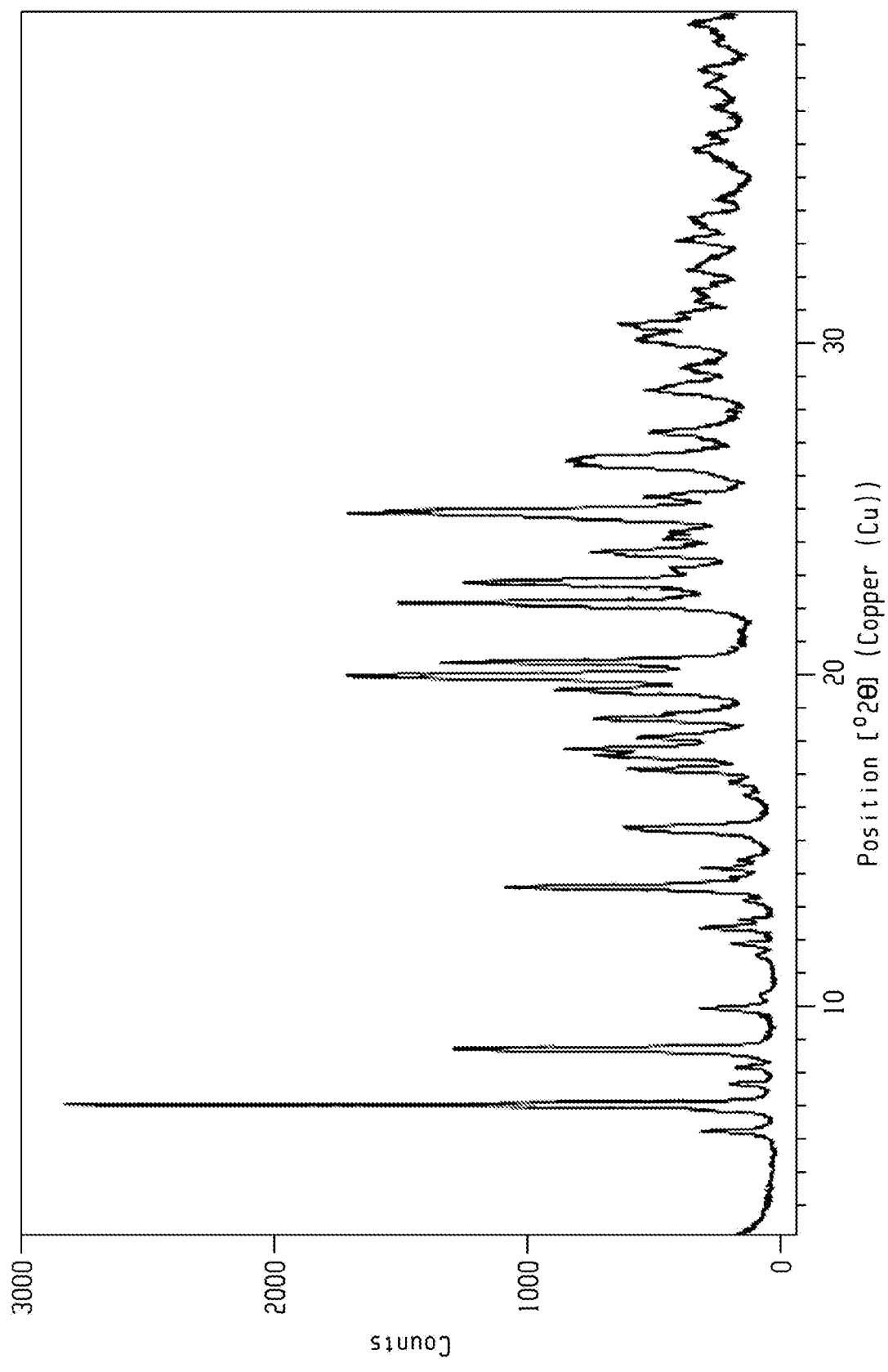

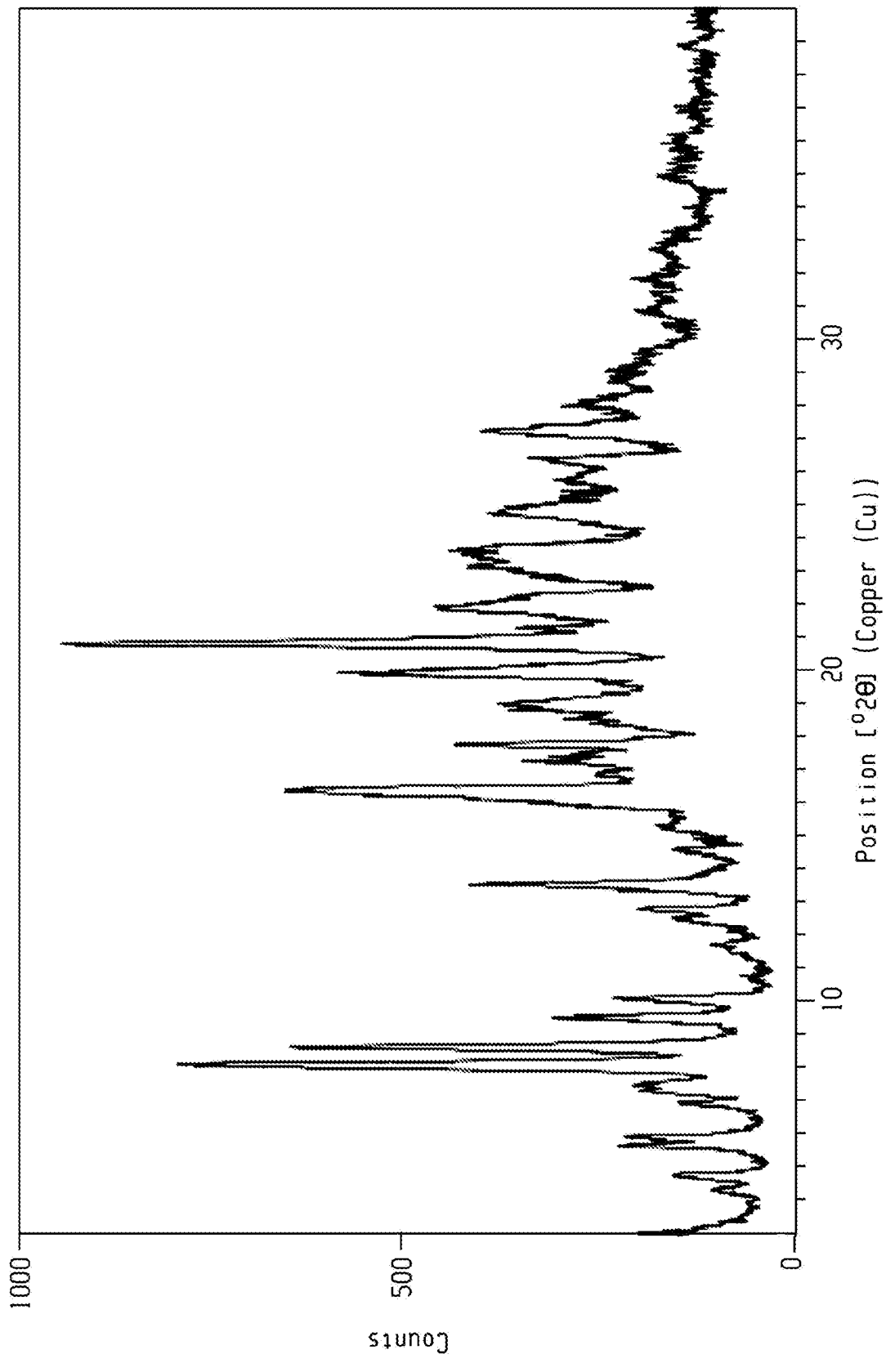
Figure 19: Remimazolam Methane Sulfonate Form 2

PROCESS FOR THE PREPARATION OF REMIMAZOLAM AND SOLID STATE FORMS OF REMIMAZOLAM SALTS

FIELD OF THE INVENTION

The present disclosure relates to novel processes for the preparation of short acting benzodiazepines as well as to novel intermediates in this process. More particularly the disclosure relates to processes and intermediates for preparation of Methyl 3-[(4S)-8-bromo-1-methyl-6-(pyridin-2-yl)-4H-imidazo[1,2-a][1,4]benzodiazepin-4-yl]propanoate, commonly known as Remimazolam. The present disclosure also relates to solid state forms of Remimazolam salts, processes for the preparation thereof, pharmaceutical formulations/compositions thereof, and methods of use thereof.

BACKGROUND

Methyl 3-[(4S)-8-bromo-1-methyl-6-(pyridin-2-yl)-4H-imidazo[1,2-a][1,4]benzodiazepin-4-yl]propanoate, is commonly known as Remimazolam (may referred to herein as Formula-I, Formula I, Compound of formula I or Compound I). Remimazolam has the following chemical structure:

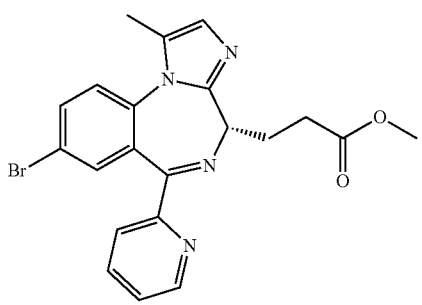

(I)

Remimazolam is developed for use in induction of anesthesia and conscious sedation for minor invasive procedures.

U.S. Pat. No. 7,485,635 (referred to herein as '635) discloses Remimazolam and process for its preparation. The process is described in scheme-1.

Scheme: 1

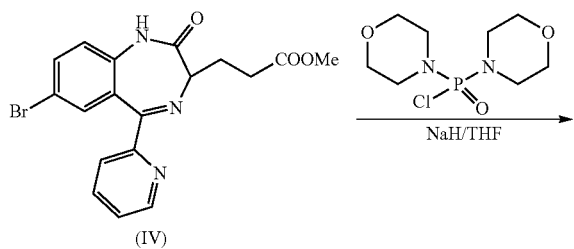

(IV)

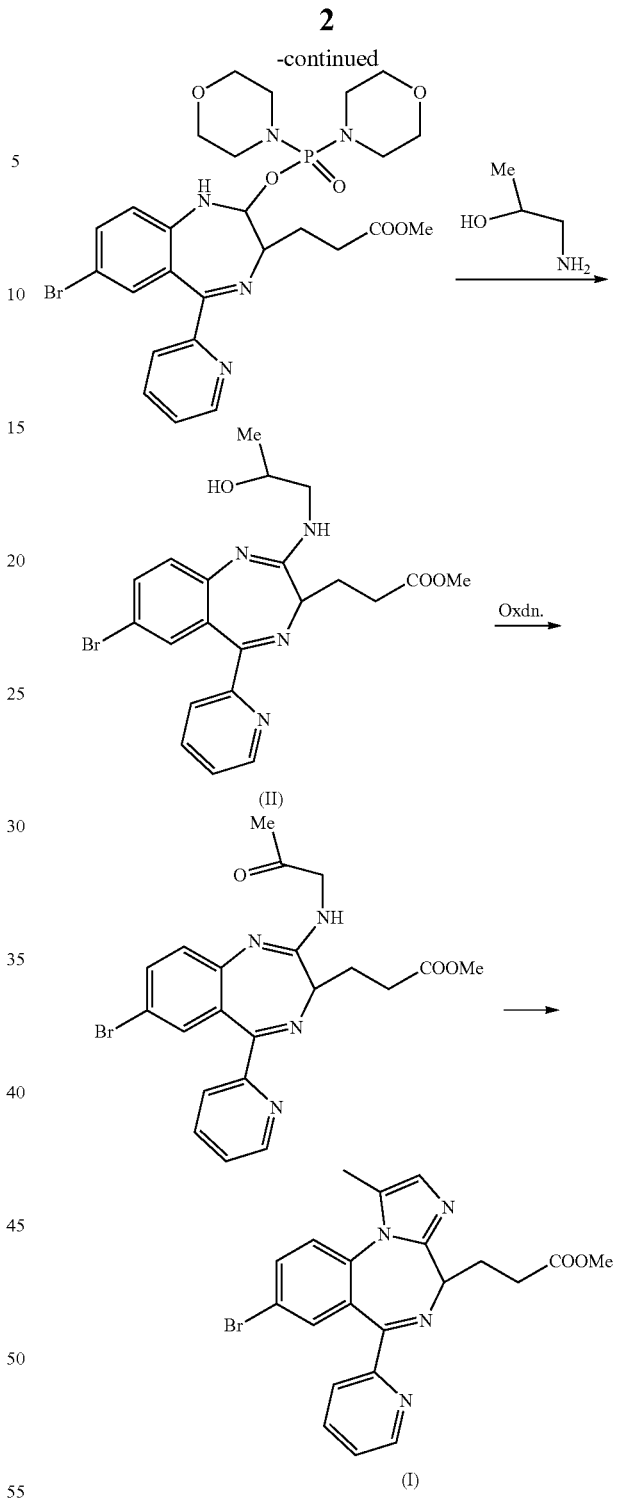

The process disclosed in '635 patent involves Swern oxidation, which needs to be carried out in the presence of dimethyl sulfoxide (DMSO) and Oxalyl chloride, and requires extremely low temperature of about −78° C., therefore this process can't be adopted for industrial scale manufacturing. In addition the process utilizes the hazardous reagents sodium hydride, Bismorpholinophosphochloridate, and Lawesson's reagent. The reported yield of this process, from intermediate IV to intermediate II is about 37% (w/w) and the overall yield is of about 33%.

U.S. Pat. No. 9,156,842 (referred to herein as '842) discloses a process for preparation of Remimazolam which utilizes Dess-Martin periodinane (DMP) for the oxidation of Compound II, an intermediate in the synthesis of Remimazolam. The reported overall yield is about 34-35% (w/w). The use of DMP is not preferred due to its potential explosive nature, its high cost and the need to use high quantity of reagent to match its high molecular weight.

The '842 patent also discloses process for preparation of compound of Compound-IV, an intermediate in the synthesis of Remimazolam, which includes tert-butyloxycarbonyl (Boc) protection and later de-protection using hydrochloric acid. This process is described in Scheme 2.

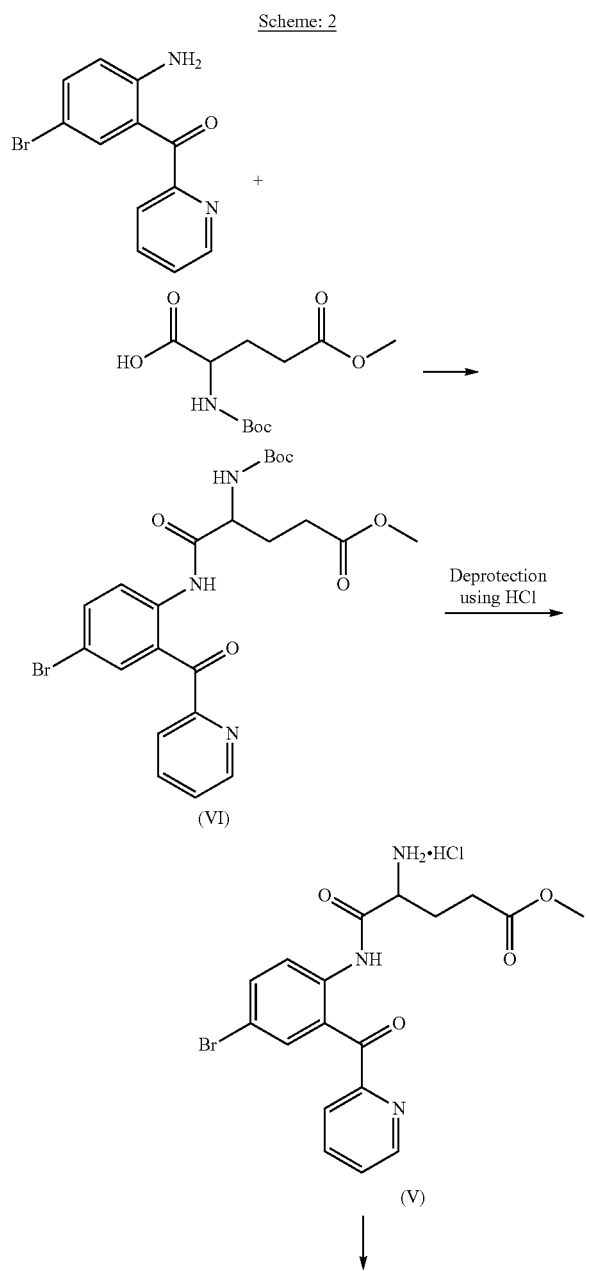

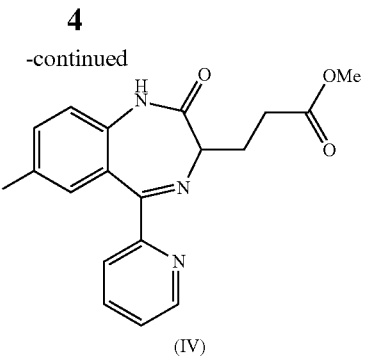

U.S. Pat. No. 9,656,987 (referred to herein as '987) teaches additional process for the preparation of Remimazolam, which includes oxidation of Compound-II in the presence N-Oxyl oxidation catalyst. The reported yield of this process, from intermediate IV to intermediate II is about 56% (w/w) and the overall yield is of about 33%. This process utilizes the hazardous reagents LDA (Lithium diisopropylamide) and bismorpholinophosphoryl chloridate and requires relatively long reaction time.

U.S. Pat. No. 9,193,730 (referred to herein as '730) discloses preparation of Besylate Salt and polymorphs of Remimazolam.

As reported, the processes disclosed in the prior art suffer from poor yield and involve hazardous chemicals, extremely tough reaction conditions, and expensive reagents. For at least these reasons there is need to develop a process for the preparation of Remimazolam, which provides the final product in high yield and purity, avoids hazardous chemicals and can be utilized in industrial scale.

Polymorphism, the occurrence of different crystal forms, is a property of some molecules and molecular complexes. A single compound, like Remimazolam or a salt thereof, may give rise to a variety of polymorphs having distinct crystal structures and physical properties like melting point, thermal behaviors (e.g. measured by thermogravimetric analysis-"TGA", or differential scanning calorimetry-"DSC"), X-ray powder diffraction (XRPD) pattern, infrared absorption fingerprint, Raman absorption fingerprint, and solid state ($^{13}$C-) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, improving the dissolution profile, or improving stability (polymorphic as well as chemical stability) and shelf-life. These variations in the properties of different salts and solid state forms may also provide improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Developing new salts and solid state forms and solvates of a pharmaceutical product can provide materials having desirable processing properties, such as ease of handling, ease of processing, storage stability, and ease of purification or as desirable intermediate crystal forms that facilitate conversion to other salts or polymorphic forms. New polymorphic forms and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life. For at least these reasons, there is a need for additional solid state forms (including solvated forms) of Remimazolam salts.

SUMMARY OF THE INVENTION

The present disclosure provides novel intermediates, their preparation and their use in the preparation of benzodiazepines. Particularly, the present disclosure provides intermediates useful for the preparation of Remimazolam.

The present disclosure provides processes for preparation of Remimazolam.

The present disclosure also provides processes for early intermediates in the synthesis of benzodiazepines, particularly, Remimazolam, namely the intermediate compound of formula III-A, III, particularly III-S, and III-13, particularly III-13S.

The present disclosure also relates to Remimazolam salts and solid state forms thereof. Particularly, it relates to crystalline forms of Remimazolam Hydrochloride, Remimazolam Mono Hydrobromide, Remimazolam Dihydrobromide, Remimazolam Fumarate, Remimazolam Oxalate, Remimazolam Sulphate, Remimazolam Methane sulfonate, Remimazolam Camphor sulfonate and Remimazolam Dibesylate.

The present disclosure also relates to the uses of solid state forms of Remimazolam salts of the present disclosure, for preparing other salts and solid state forms of Remimazolam.

The present disclosure also encompasses the uses of the above described solid state forms of Remimazolam salts for the preparation of pharmaceutical compositions and/or formulations.

In another embodiment, the present disclosure encompasses pharmaceutical compositions comprising the above described solid state forms of Remimazolam salts.

In yet another embodiment, the present disclosure encompasses pharmaceutical formulations comprising the above described solid state forms of Remimazolam salts, and at least one pharmaceutically acceptable excipient.

The present disclosure further encompasses processes to prepare said pharmaceutical formulations of solid state forms of Remimazolam salts comprising combining any one of the above described solid state forms of Remimazolam salts, or pharmaceutical compositions comprising them, and at least one pharmaceutically acceptable excipient.

The solid state forms of Remimazolam salts defined herein as well as the pharmaceutical compositions and formulations of the solid state form of the Remimazolam salts can be used as medicaments, particularly for induction of anesthesia and conscious sedation for minor invasive procedures. The present disclosure provides a method of inducing anesthesia and conscious sedation for minor invasive procedures comprising administering a therapeutically effective amount of any of the solid state form of Remimazolam salts of the present disclosure, or at least one of the above pharmaceutical compositions or formulations, to a subject which needs induction of anesthesia and conscious sedation for minor invasive procedures, or otherwise in need of the treatment.

The present disclosure also provides the uses of the solid state forms of Remimazolam salts of the present disclosure, or at least one of the above pharmaceutical compositions or formulations, for the manufacture of medicaments for induction of anesthesia and conscious sedation for minor invasive procedures.

In another aspect, the present disclosure encompasses the above solid state forms of Remimazolam salts for use in medicine, preferably for induction of anesthesia and conscious sedation for minor invasive procedures.

BRIEF DESCRIPTION OF THE FIGURES

FIG. 1 shows Mass Spectra of the compound of formula III-S.

FIG. 2 shows $^1$H-NMR Spectra of the compound of formula III-S.

FIG. 3 shows $^{13}$C-NMR Spectra of the compound of formula III-S.

FIG. 4 shows IR Spectra of the compound of formula III-S.

FIG. 5 shows Mass Spectra of the compound of formula III-13S.

FIG. 6 shows $^1$H-NMR Spectra of the compound of formula III-13S.

FIG. 7 shows $^{13}$C-NMR Spectra of the compound of formula III-13S.

FIG. 8 shows IR Spectra of the compound of formula III-13S.

FIG. 9 shows an XRPD pattern of Form 1 of Remimazolam Hydrochloride.

FIG. 10 shows an XRPD pattern of Form 1 of Remimazolam Dihydrobromide.

FIG. 11 shows an XRPD pattern of Form 1 of Remimazolam Fumarate.

FIG. 12 shows an XRPD pattern of Form 1 of Remimazolam Oxalate.

FIG. 13 shows an XRPD pattern of Form 1 of Remimazolam Sulphate.

FIG. 14 shows an XRPD pattern of Form 1 of Remimazolam Methane Sulfonate.

FIG. 15 shows an XRPD pattern of Form 1 of Remimazolam Camphor Sulfonate.

FIG. 16 shows an XRPD pattern of Form 1 of Remimazolam Dibesylate.

FIG. 17 shows an XRPD pattern of Form 2 of Remimazolam Camphor Sulfonate.

FIG. 18 shows an XRPD pattern of Form 1 of Remimazolam Mono Hydrobromide.

FIG. 19 shows an XRPD pattern of Form 2 of Remimazolam Methane Sulfonate.

DETAILED DESCRIPTION OF THE INVENTION

The present disclosure relates to novel processes for preparation of short acting benzodiazepines as well as to novel intermediates in this process. More particularly the disclosure relates to processes and intermediates for preparation of Methyl 3-[(4S)-8-bromo-1-methyl-6-(pyridin-2-yl)-4H-imidazo[1,2-a][1,4]benzodiazepin-4-yl]propanoate, commonly known as Remimazolam.

The process of the present disclosure provides the final product, Remimazolam, in excellent yield and purity, avoids the use of hazardous reagents, such as Bismorpholinophosphoryl chloridate and is performed in convenient environment and conditions, therefore it is suitable for use in industrial scale.

The present disclosure relates also to solid state forms of Remimazolam salts, to processes for preparation thereof and to pharmaceutical compositions and formulations comprising these solid state forms and/or combinations thereof.

The solid state forms of Remimazolam salts according to the present disclosure may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents, adhesive tendencies and advantageous processing and handling characteristics such as compressibility, and bulk density.

As used herein, the term "isolated" in reference to solid state forms of novel intermediates and Remimazolam of the present invention corresponds to a solid state form of novel intermediates and Remimazolam that is physically separated from the reaction mixture in which it is formed.

As used herein, the term "isolated" in reference to the solid state forms of Remimazolam salts of the present disclosure corresponds to solid state form of Remimazolam salt that is physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

The amount of solvent employed in a chemical process, e.g., a reaction or a crystallization may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding methyl tert-butyl ether (MTBE) (1.5 v/v) to a 100 ml reaction mixture would indicate that 150 mL of methyl tert-butyl ether (MTBE) was added.

As used herein, the term "reduced pressure" refers to a pressure of about 10 mbar to about 500 mbar, or about 10 mbar to about 50 mbar.

A crystal form may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

A crystal form of Remimazolam salt, referred to herein as being characterized by graphical data "as depicted in" a Figure will thus be understood to include any crystal form of the Remimazolam salt, characterized with the graphical data having such small variations, as are well known to the skilled person, in comparison with the Figure.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD.

Thus, solid state form of Remimazolam salt described herein as substantially free of any other solid state forms would be understood to contain greater than about 80% (w/w), greater than about 90% (w/w), greater than about 95% (w/w), greater than about 98% (w/w), greater than about 99% (w/w), or about 100% (w/w) of the subject solid state form of Remimazolam salt.

In some embodiments of the disclosure, the described solid state forms of Remimazolam salt may contain from about 1% to about 20% (w/w), from about 5% to about 20% (w/w), or from about 5% to about 10% (w/w) of one or more other solid state forms of Remimazolam salt.

As used herein, unless stated otherwise, XRPD peaks reported herein are preferably measured using CuKα radiation, λ=1.5418 Å, preferably, XRPD peaks reported herein are measured using CuK α radiation, λ=1.5418 Å, at a temperature of 25±3° C.

As used herein, and unless stated otherwise, the term "anhydrous" in relation to a crystalline Remimazolam salt relates to a crystalline Remimazolam salt which does not include any crystalline water (or other solvents) in a defined, stoichiometric amount within the crystal. Moreover, an "anhydrous" form does not contain more than about 1% (w/w) of either water or organic solvents as measured for example by TGA.

The term "solvate", as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein the term non-hygroscopic in relation to a crystalline form of Remimazolam salt, refers to less than about 1.0% (w/w) absorption of water at about 25° C. and about 80% relative humidity (RH), by the crystalline form of Remimazolam salt as determined for example by TGA. Water can be for example atmospheric water.

The present disclosure provides efficient process for preparation of Remimazolam and Remimazolam intermediates.

In one embodiment, the present disclosure provides novel compound of Formula III-A, its salts, solvates, hydrates or isomers thereof.

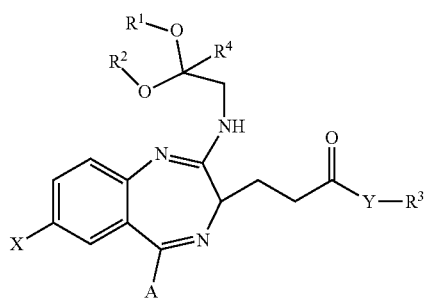

(III-A)

wherein, $R^1$ and $R^2$ are independently Alkyl or they are connected to form a cyclic ring, $R^3$ and $R^4$ are independently H, alkyl, acyl, vinyl or allyl, X is any halogen, Y is O, S or N; or Y is $NR^5$ wherein $R^5$ is H, alkyl, acyl, vinyl or allyl; and A is alkyl or aliphatic, aromatic or heterocyclic ring.

Preferably, as used herein, alkyl includes $C_1$-$C_{12}$ straight chain or branched alkyl, specifically $C_1$-$C_8$, preferably $C_1$-$C_3$, more preferably $C_1$, i.e. methyl.

Preferably, as used herein, ring includes $C_1$-$C_{12}$, specifically $C_1$-$C_8$.

Preferably, A is 2-pyridinyl.

In another embodiment, the present disclosure provides a process for preparation of compound of Formula-III-A and its salts, solvates, hydrates or isomers thereof. The process comprises preparing the compound of formula-IV-A and converting it to compound of Formula-III-A.

In yet another embodiment, the present disclosure provides use of the compound of formula-III-A in the preparation of compound of Formula-I-A, as well as a process of preparation of compound of Formula-I-A comprising preparing the compound of formula-III-A or its salts, solvates, hydrates or isomers thereof and converting it to the compound of Formula-I-A.

In specific embodiment, the present disclosure provides a process for preparing benzodiazepines of formula I-A, comprising:
a. reacting the compound of formula IV-A and an amino ketal compound in presence of a carbonyl activating group to obtain the compound of formula III-A; and
b. converting the compound of formula III-A to the compound of formula I-A by deprotecting the ketal followed by cyclization in acidic condition.

The amino ketal compounds may be prepared from corresponding amino ketone and diols wherein diols having hydroxyl functional groups separated by C1 to C8 carbon chain which may be saturated, unsaturated, substituted or cyclic. Preferred examples of Amino ketal compounds are (2-methyl-1,3-dioxolan-2-yl)methanamine; (2,5,5-trimethyl-1,3-dioxan-2-yl)methanamine, 1-amino-2,2-dimethoxypropane etc.

The carbonyl activating group can be selected from the group comprising of triflic anhydride, triflic acid, benzene sulfonic acid, Toluene sulfonic acid, Methane sulfonic acid and the like.

The process can be summarized by the following Scheme-3:

Scheme: 3

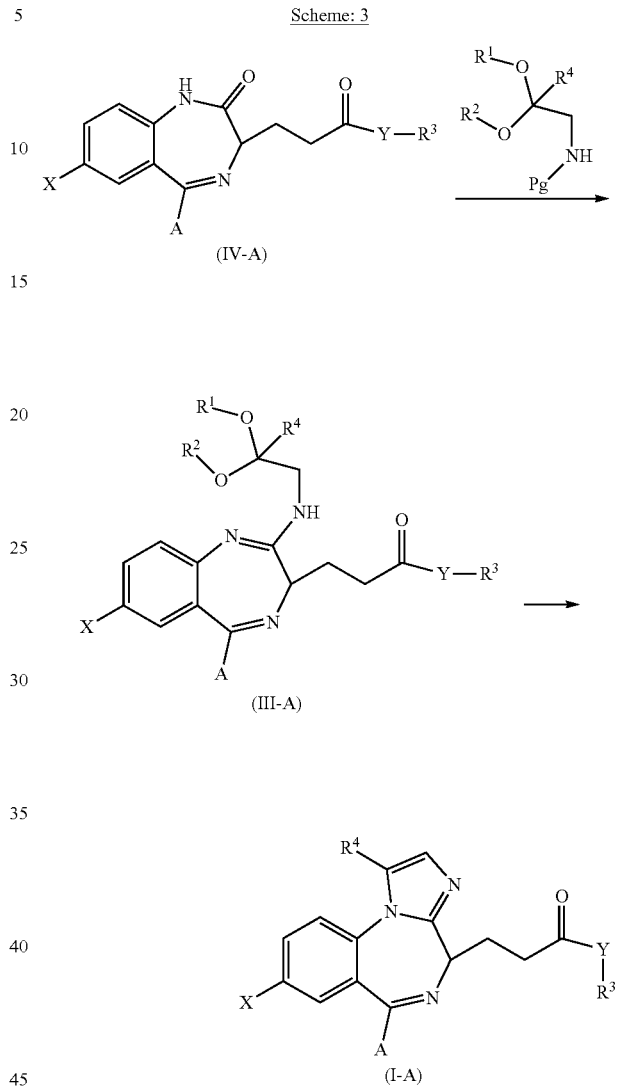

wherein, $R^1$ and $R^2$ are independently Alkyl or they are connected to form a cyclic ring, $R^3$ and $R^4$ are independently H, alkyl, acyl, vinyl or allyl, X is any halogen, Y is O, S or N, or Y is $NR^5$ wherein $R^5$ is H, alkyl, acyl, vinyl or allyl, A is alkyl or aliphatic, aromatic or heterocyclic ring; and Pg is H, amino protecting group or counter ion.

The above process can be done either as a one pot reaction, meaning, the Compound of formula I-A can be prepared from compound of formula IV-A without isolating compound of formula III-A. Alternatively, the compound of formula III-A can be isolated prior to its conversion to compound of formula I-A. Preferably, compound III-A is obtained in a crystalline form.

In specific embodiment, the present disclosure provides novel compound of formula III, its salts, solvates, hydrates or isomers thereof:

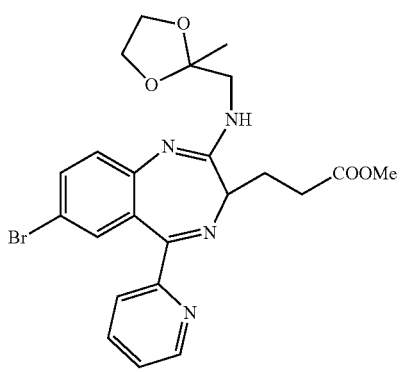

(III)

The compound of formula III can be isolated, either as crystalline or non-crystalline form. Preferably, compound III is crystalline.

The compound of formula III may be a racemic mixture, or enantiomerically pure. Preferably, the compound of formula III is in S-configuration, i.e. compound of formula III-S:

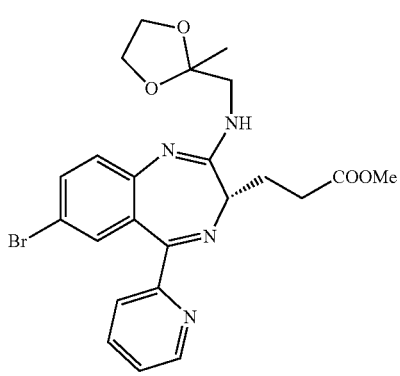

(III-S)

The compound of formula III-S is typically characterized by mass spectra as shown in FIG. 1, or by $^1$H-NMR as shown in FIG. 2, or by combination thereof.

Crystalline compound of formula III-S may be characterized by data selected from one or more of the following: $^{13}$C-NMR Spectra of the compound of formula III-S as shown in FIG. 3; IR Spectra of the compound of formula III-S as shown in FIG. 4; and combinations of these data.

The compound of Formula-III, its salts, solvates, hydrates or isomer thereof can be prepared by a process comprising preparing the compound of formula-IV and converting it to compound of Formula-III.

The compound of Formula-III, its salts, solvates, or hydrates thereof are useful in the preparation of Remimazolam, the compound of formula I.

In another embodiment the present disclosure provides a process for preparing Remimazolam comprising:
 a. reacting the compound of formula IV and an amino ketal compound in presence of a carbonyl activating group to obtain the compound of formula III; and
 b. converting the compound of formula III to the compound of formula I, by deprotecting the ketal followed by cyclization in acidic conditions.

Amino ketal compound and carbonyl activating group are as defined above, preferably the amino ketal is 2-methyl-1,3-dioxolan-2-yl)methanamine.

The process can be summarized by the following Scheme-4:

Scheme: 4

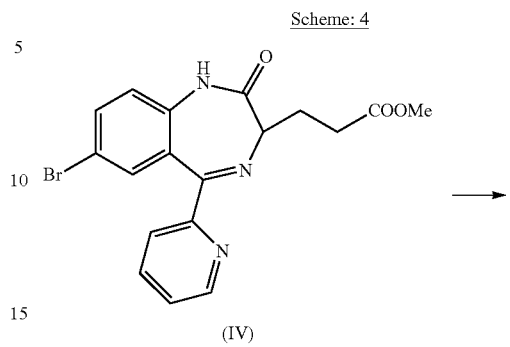

(IV)

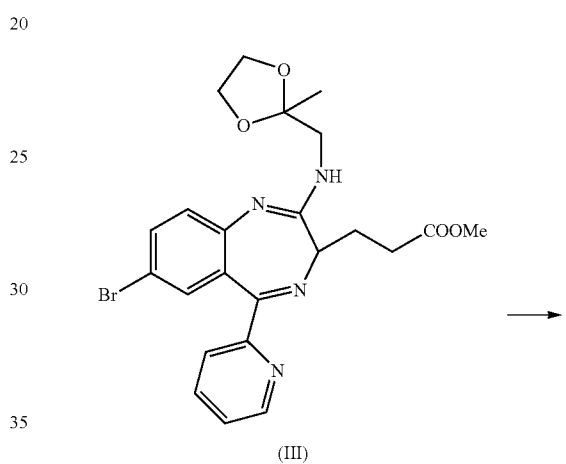

(III)

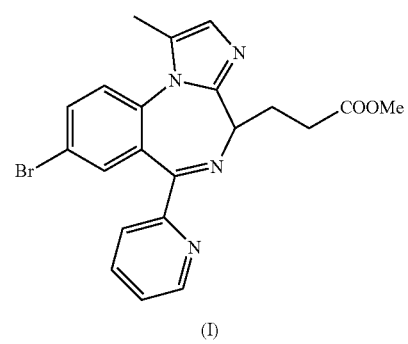

(I)

The above process can be done either as a one pot reaction, meaning, the compound of formula I can be prepared from compound of formula IV without isolating compound of formula III. Alternatively, the compound of formula III can be isolated prior to its conversion to compound of formula I.

In specific embodiment, the present disclosure provides novel compound of formula III-13, its salts, solvates, hydrates or isomers thereof:

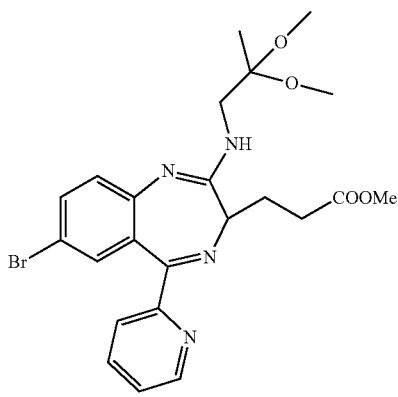

(III-13)

The compound of formula III-13 can be isolated, either as crystalline or non-crystalline form. Preferably, compound III-13 is crystalline.

The compound of formula III-13 may a racemic mixture, or enantiomerically pure. Preferably, the compound of formula III-13 is in S-configuration, i.e. compound of formula III-13 S:

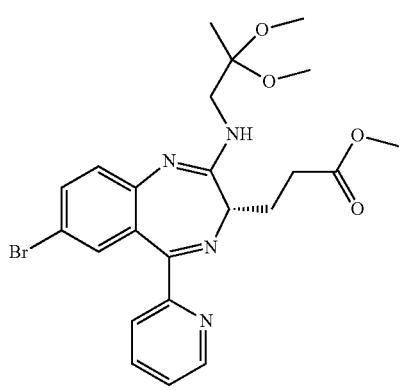

(III-13S)

The compound of formula III-13 S is typically characterized by mass spectra as shown in FIG. 5, or by $^1$H-NMR as shown in FIG. 6, or by combination thereof.

Crystalline compound of formula III-13 S may be characterized by data selected from one or more of the following: $^{13}$C-NMR Spectra of the compound of formula III-13S as shown in FIG. 7; IR Spectra of the compound of formula III-13S as shown in FIG. 8; and combinations of these data.

The compound of Formula-III-13, its salts, solvates, hydrates or isomer thereof can be prepared by a process comprising preparing the compound of formula-IV and converting it to compound of Formula-III-13.

The compound of Formula-III-13, its salts, solvates, or hydrates thereof are useful in the preparation of Remimazolam, the compound of formula I.

In another embodiment the present disclosure provides a process for preparing Remimazolam comprising:
a. reacting the compound of formula IV and an amino ketal compound (such as 1-amino-2,2-dimethoxypropane) in presence of a carbonyl activating group to obtain the compound of formula III-13; and
b. converting the compound of formula III-13 to the compound of formula I, by deprotecting the ketal followed by cyclization in acidic conditions.

Amino ketal compound and carbonyl activating group are as defined above.

The process can be summarized by the following Scheme-4a:

Scheme: 4a

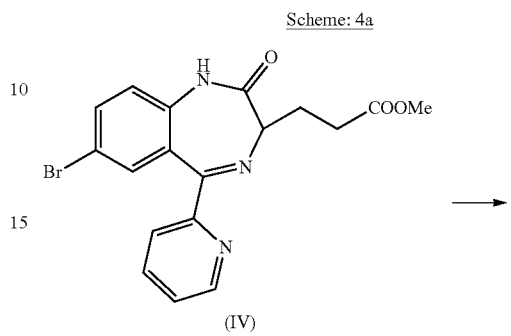

(IV)

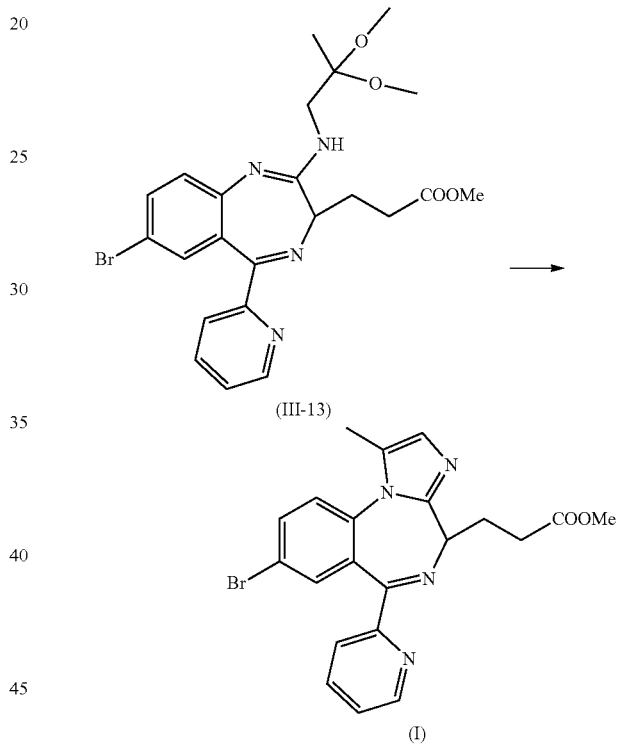

The above process can be done either as a one pot reaction, meaning, the compound of formula I can be prepared from compound of formula IV without isolating compound of formula III-13. Alternatively, the compound of formula III-13 can be isolated prior to its conversion to compound of formula I.

In another embodiment, the present disclosure provides additional processes for preparation of Remimazolam, comprising reacting the compound of formula IV-A and amino-alcohol, such as 1-Aminopropan-2-ol in the presence of triflic anhydride and halopyridine, to form the compound of formula II-A. This process avoids the use of hazardous reagent, can be performed at relatively short reaction time and provides the compound of formula II-A in high yield, of at least 80% (w/w).

The process can be summarized by the following Scheme-5:

Scheme: 5

[Structure (IV-A): benzodiazepinone with X substituent and side chain -CH2CH2C(=O)-Y-R3]

Triflic Anhydride
Halo Pyridine
→

Pg1-O-CH(R4)-CH2-NH-Pg

[Structure (II-A)]

Scheme: 6

[Structure (IV): 7-bromo benzodiazepinone with pyridin-2-yl and -CH2CH2COOMe]

Triflic Anhydride
2-Bromo pyridine
→

HO-CH(Me)-CH2-NH2

[Structure (II)]

wherein as R³ and R⁴ are independently H, alkyl, acyl, vinyl or allyl,

X is any halogen,

Y is O, S or N, or Y is NR⁵ wherein R⁵ is H, alkyl, acyl, vinyl or allyl,

A is alkyl or aliphatic, aromatic or heterocyclic ring, and

Pg₁ is H or any hydroxyl protecting group.

Preferably, as used herein, the term "Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2nd ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("BOC"), trimethylsilyl ("TMS"), 2-trimethylsilylethanesulfonyl, ("SES"), trityl and substituted trityl groups, allyloxycarbonyl, 9-fluorenylmethyloxycarbonyl ("FMOC"), nitro-veratryloxycarbonyl ("NVOC") and the like.

Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

More specifically the present invention relates to the process of preparation of compound of Formula-II from the compound of formula-IV as described in Scheme-6.

In yet another embodiment, the present disclosure provides the preparation of early intermediates in the synthesis of Remimazolam, namely the preparation of the compound of formula-V-A. The process comprises de-protection of the compound of formula VI using a suitable acid, excluding hydrochloric acid. The process can be summarized by the following Scheme-7:

Scheme: 7

[Structure (VI)]

→

-continued

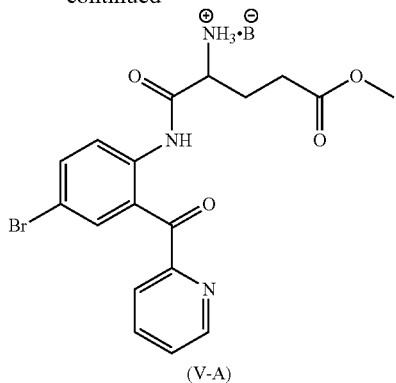

(V-A)

wherein B⁻ is anion of corresponding acid which is sufficient for the de-protection of -Boc with the proviso that B⁻ is not Cl⁻. Preferably, the acid is triflic acid and B⁻ is $CF_3SO_3^-$ Remimazolam prepared by the above described processes can be used to prepare solid state forms of Remimazolam, Remimazolam salts and their solid state forms thereof.

The present disclosure comprises a crystalline form of Remimazolam Hydrochloride designated as Form 1. The crystalline Form 1 of Remimazolam Hydrochloride can be characterized by data selected from one or more of the following: an XRPD pattern having peaks at 9.0, 12.5, 13.5, 20.8 and 25.2 degrees two theta ±0.2 degrees two theta; an XRPD pattern substantially as depicted in FIG. 9; or combinations of these data. Crystalline Form 1 of Remimazolam Hydrochloride may be further characterized by data selected from one or more of the following: an XRPD pattern having peaks at 9.0, 12.5, 13.5, 20.8 and 25.2 degrees two theta ±0.2 degrees two theta; and also having one, two, three, four or five additional peaks selected from 16.0, 19.1, 19.8, 21.7 and 27.7 degrees two theta ±0.2 degrees two theta; or combinations of these data.

The present disclosure further comprises a crystalline form of Remimazolam Dihydrobromide designated as Form 1. The crystalline Form 1 of Remimazolam Dihydrobromide can be characterized by data selected from one or more of the following: an XRPD pattern having peaks at 8.1, 10.3, 12.7, 15.1, 17.0, 20.6, 22.7 and 25.2 degrees two theta ±0.2 degrees two theta; an XRPD pattern substantially as depicted in FIG. 10; or combinations of these data. Crystalline Form 1 of Remimazolam Dihydrobromide may be further characterized by data selected from one or more of the following: an XRPD pattern having peaks at 8.1, 10.3, 12.7, 15.1, 17.0, 20.6, 22.7 and 25.2 degrees two theta ±0.2 degrees two theta; and also having one, two, three, four, five or six additional peaks selected from 13.7, 16.6, 17.6, 21.1, 23.5 and 26.6 degrees two theta ±0.2 degrees two theta; or combinations of these data.

The present disclosure further comprises a crystalline form of Remimazolam Mono hydrobromide designated as Form 1. The crystalline Form 1 of Remimazolam Mono hydrobromide can be characterized by data selected from one or more of the following: an XRPD pattern having peaks at 7.1, 8.7, 13.6, 22.2 and 24.9 degrees two theta ±0.2 degrees two theta; an XRPD pattern substantially as depicted in FIG. 18; or combinations of these data. Crystalline Form 1 of Remimazolam Mono hydrobromide may be further characterized by data selected from one or more of the following: an XRPD pattern having peaks at 7.1, 8.7, 13.6, 22.2 and 24.9 degrees two theta ±0.2 degrees two theta; and also having one, two, three, four or five additional peaks selected from 15.4, 19.6, 20.0, 20.4 and 22.4 degrees two theta ±0.2 degrees two theta; or combinations of these data.

Crystalline Form 1 of Remimazolam Mono hydrobromide may have advantageous properties, as detailed above. Particularly, crystalline Form 1 of Remimazolam Mono hydrobromide is stable for a period of at least 24 hours at 80% relative humidity (RH) at room temperature (RT) in open Petri dish; and it has improved kinetic water solubility as well as improved solubility in various pH ranges.

The present disclosure also comprises a crystalline form of Remimazolam Fumarate designated as Form 1. The crystalline Form 1 of Remimazolam Fumarate can be characterized by data selected from one or more of the following: an XRPD pattern having peaks at 7.0, 9.0, 10.2, 12.4, 14.1, 17.3, 20.2, 24.1 and 26.2 degrees two theta ±0.2 degrees two theta; an XRPD pattern substantially as depicted in FIG. 11; or combinations of these data. Crystalline Form 1 of Remimazolam Fumarate may be further characterized by data selected from one or more of the following: an XRPD pattern having peaks at 7.0, 9.0, 10.2, 12.4, 14.1, 17.3, 20.2, 24.1 and 26.2 degrees two theta ±0.2 degrees two theta; and also having one, two, three, four or five additional peaks selected from 9.6, 11.9, 14.8, 16.7 and 20.6 degrees two theta ±0.2 degrees two theta; or combinations of these data.

The present disclosure also comprises a crystalline form of Remimazolam Oxalate designated as Form 1. The crystalline Form 1 of Remimazolam Oxalate can be characterized by data selected from one or more of the following: an XRPD pattern having peaks at 6.7, 8.7, 11.3, 13.3, 15.2, 16.9, 20.9 and 25.9 degrees two theta ±0.2 degrees two theta; an XRPD pattern substantially as depicted in FIG. 12; or combinations of these data. Crystalline Form 1 of Remimazolam Oxalate may be further characterized by data selected from one or more of the following: an XRPD pattern having peaks at 6.7, 8.7, 11.3, 13.3, 15.2, 16.9, 20.9 and 25.9 degrees two theta ±0.2 degrees two theta; and also having one, two, three, four or five additional peaks selected from 7.5, 12.5, 19.7, 20.0 and 20.4 degrees two theta ±0.2 degrees two theta; or combinations of these data.

The present disclosure also comprises a crystalline form of Remimazolam Sulphate designated as Form 1. The crystalline Form 1 of Remimazolam Sulphate can be characterized by data selected from one or more of the following: an XRPD pattern having peaks at 10.2, 13.7, 15.7, 16.5, 21.1, 22.3 and 27.6 degrees two theta ±0.2 degrees two theta; an XRPD pattern substantially as depicted in FIG. 13; or combinations of these data. Crystalline Form 1 of Remimazolam Sulphate may be further characterized by data selected from one or more of the following: an XRPD pattern having peaks at 10.2, 13.7, 15.7, 16.5, 21.1, 22.3 and 27.6 degrees two theta ±0.2 degrees two theta; and also having one, two, three, or four additional peaks selected from 15.0, 21.7, 23.6 and 24.3 degrees two theta ±0.2 degrees two theta; or combinations of these data.

The present disclosure also comprises a crystalline form of Remimazolam Methane Sulfonate (i.e. mesylate) designated as Form 1. The crystalline Form 1 of Remimazolam Methane Sulfonate can be characterized by data selected from one or more of the following: an XRPD pattern having peaks at 4.3, 5.6, 8.7, 13.3, 16.3, 19.8 and 22.0 degrees two theta ±0.2 degrees two theta; an XRPD pattern substantially as depicted in FIG. 14; or combinations of these data. Crystalline Form 1 of Remimazolam Methane Sulfonate may be further characterized by data selected from one or more of the following: an XRPD pattern having peaks at 4.3, 5.6, 8.7, 13.3, 16.3, 19.8 and 22.0 degrees two theta ±0.2 degrees two theta; and also having one, two, three, four, five or six additional peaks selected from 5.9, 8.2, 16.8, 18.8, 22.9 and 24.8 degrees two theta ±0.2 degrees two theta; or combinations of these data.

The present disclosure also comprises a crystalline form of Remimazolam Methane Sulfonate (i.e. mesylate) designated as Form 2. The crystalline Form 2 of Remimazolam Methane Sulfonate can be characterized by data selected from one or more of the following: an XRPD pattern having peaks at 5.0, 9.5, 10.1, 20.9 and 27.3 degrees two theta ±0.2 degrees two theta; an XRPD pattern substantially as depicted in FIG. 19; or combinations of these data. Crystalline Form 2 of Remimazolam Methane Sulfonate may be further characterized by data selected from one or more of the following: an XRPD pattern having peaks at 5.0, 9.5, 10.1, 20.9 and 27.3 degrees two theta ±0.2 degrees two theta; and also having one, two, three or four additional peaks selected from 16.3, 18.5, 18.9 and 20.5 degrees two theta ±0.2 degrees two theta; or combinations of these data.

Crystalline Form 2 of Remimazolam Methane Sulfonate may be a hydrate, preferably a mono hydrate.

Crystalline Form 2 of Remimazolam Methane Sulfonate may have advantageous properties, as detailed above. Particularly, crystalline Form 2 of Remimazolam Methane Sulfonate is stable for a period of at least 24 hours at 80% relative humidity (RH) at room temperature (RT) in open Petri dish; and it has improved kinetic water solubility as well as improved solubility in various pH ranges.

The present disclosure also comprises a crystalline form of Remimazolam Camphor Sulfonate (i.e. camsylate) designated as Form 1. The crystalline Form 1 of Remimazolam Camphor Sulfonate can be characterized by data selected from one or more of the following: an XRPD pattern having peaks at 6.5, 11.8, 12.9, 15.1, 17.7, 19.3, 21.2 and 24.0 degrees two theta ±0.2 degrees two theta; an XRPD pattern substantially as depicted in FIG. 15; or combinations of these data. Crystalline Form 1 of Remimazolam Camphor Sulfonate may be further characterized by data selected from one or more of the following: an XRPD pattern having peaks at 6.5, 11.8, 12.9, 15.1, 17.7, 19.3, 21.2 and 24.0 degrees two theta ±0.2 degrees two theta; and also having one, two, three or four additional peaks selected from 14.3, 16.5, 19.6 and 21.5 degrees two theta ±0.2 degrees two theta; or combinations of these data.

The present disclosure also comprises a crystalline form of Remimazolam Camphor Sulfonate (i.e. camsylate) designated as Form 2. The crystalline Form 2 of Remimazolam Camphor Sulfonate can be characterized by data selected from one or more of the following: an XRPD pattern having peaks at 5.7, 10.0, 15.4, 16.3 and 18.1 degrees two theta ±0.2 degrees two theta; an XRPD pattern substantially as depicted in FIG. 17; or combinations of these data. Crystalline Form 2 of Remimazolam Camphor Sulfonate may be further characterized by data selected from one or more of the following: an XRPD pattern having peaks at 5.7, 10.0, 15.4, 16.3 and 18.1 degrees two theta ±0.2 degrees two theta; and also having one, two, three, four or five additional peaks selected from 11.4, 14.9, 19.3, 20.6 and 25.1 degrees two theta ±0.2 degrees two theta; or combinations of these data.

Crystalline Form 2 of Remimazolam Camphor Sulfonate may be a hydrate, preferably a hemi hydrate.

Crystalline Form 2 of Remimazolam Camphor Sulfonate may have advantageous properties, as detailed above. Particularly, crystalline Form 2 of Remimazolam Camphor Sulfonate is stable for a period of at least 24 hours at 80% relative humidity (RH) at room temperature (RT) in open Petri dish; it possesses higher bulk density and improved compressibility properties compared to Remimazolam besylate. The improved compressibility properties may indicate better flow properties.

The present disclosure also comprises a crystalline form of Remimazolam dibesylate designated as Form 1. The crystalline Form 1 of Remimazolam dibesylate can be characterized by data selected from one or more of the following: an XRPD pattern having peaks at 7.2, 12.5, 20.4, 21.8 and 22.9 degrees two theta ±0.2 degrees two theta; an XRPD pattern substantially as depicted in FIG. 16; or combinations of these data. Crystalline Form 1 of Remimazolam dibesylate may be further characterized by data selected from one or more of the following: an XRPD pattern having peaks at 7.2, 12.5, 20.4, 21.8 and 22.9 degrees two theta ±0.2 degrees two theta; and also having one, two, three, four or five additional peaks selected from 14.6, 15.0, 17.6, 18.3 and 24.7 degrees two theta ±0.2 degrees two theta; or combinations of these data.

The present disclosure provides uses of the solid state forms of Remimazolam salts of the present disclosure, for preparing other solid state forms of Remimazolam, Remimazolam salts, and solid state forms thereof.

The present disclosure also provides process for preparing solid state forms of Remimazolam, Remimazolam salts or solid state forms thereof, said process comprises preparing any one or a combination of the solid state forms of Remimazolam salts, according to the present disclosure, and converting them to Remimazolam or solid state forms thereof, or to Remimazolam salt and solid state forms thereof. The conversion can be done, for example, by reacting solid state form of Remimazolam salt described herein with a suitable base to obtain Remimazolam base, and may further comprises reacting the Remimazolam base with a suitable acid to prepare the corresponding acid addition salt.

The present disclosure also provides the use of any one of the above described solid state forms of Remimazolam salts, or combinations thereof, for the preparation of pharmaceutical compositions and/or formulations.

The present disclosure further provides pharmaceutical compositions comprising any one of the above described solid state forms of Remimazolam salts, or combinations thereof.

In yet another embodiment, the present disclosure encompasses pharmaceutical formulations comprising any one of the above described solid state forms of Remimazolam salts, and/or combinations thereof, and at least one pharmaceutically acceptable excipient.

The present disclosure moreover encompasses processes to prepare said formulations of solid state forms of Remimazolam salts comprising combining any one of the above solid state forms of Remimazolam salts, and/or combinations thereof, and at least one pharmaceutically acceptable excipient.

In another embodiment, the present disclosure encompasses any one of the above described solid state forms of Remimazolam salts, or combinations thereof, for use in medicine, preferably for use in induction of anesthesia and conscious sedation for minor invasive procedures.

The present disclosure also provides methods of induction of anesthesia and conscious sedation for minor invasive procedures, comprising administering a therapeutically effective amount of any one of the solid state forms of Remimazolam salts of the present disclosure or combinations thereof, or at least one of the above pharmaceutical compositions or formulations, to a subject induction of anesthesia and conscious sedation for minor invasive procedures, or otherwise in need of the treatment.

The present disclosure also provides the use of any one of the solid state forms of Remimazolam salts of the present disclosure, or combinations thereof, or at least one of the above pharmaceutical compositions or formulations, for the manufacture of a medicament for use in induction of anesthesia and conscious sedation for minor invasive procedures.

The present disclosure further provides the solid state forms of Remimazolam salts of the present disclosure, or combinations thereof, or at least one of the above pharmaceutical compositions or formulations for use in medicine, especially for use in induction of anesthesia and conscious sedation for minor invasive procedures.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

Analytical Tools:
1) NMR: Bruker 400 MHz, Avance-III, Sample preparation: About 10 mg in DMSO-D6 solution.
2) IR: Bruker Tensor 27, Sample Preparation:KBr Pellet (1:100=sample:KBr ratio).
3) Mass: Shimadzu LCMS-IT-TOF, Sample Preparation=5 mg in 5 ml Methanol.

Analytical Methods

X-Ray Powder Diffraction Pattern ("XRPD")-Method 1:

X-ray diffraction was performed on X-Ray powder diffractometer: X'Pert PRO PANalytical; CuKα radiation (λ=1.5418 Å); PIXcel detector; laboratory temperature 22-25° C.; the samples were gently ground by means of mortar and pestle in order to obtain a fine powder.

Measurement Parameters:
Scan range (°): 3.000-40.001
Step size (°): 0.0131
Time per Step (s): 66.3
No. of steps: 2818
Scan mode: Continuous
Sample spinning: Without Spin
Sample holder: PW1811/16 ring holder with zero background plate X-Ray Powder Diffraction Pattern ("XRPD")-Method 2:

X-ray diffraction was performed on X-Ray powder diffractometer: Bruker D8 Advance; CuK_ radiation (λ=1.5418 Å); Lynx eye detector; laboratory temperature 22-25° C.; PMMA specimen holder ring. Prior to analysis, the samples were gently ground by means of mortar and pestle in order to obtain a fine powder. The ground sample was adjusted into a cavity of the sample holder and the surface of the sample was smoothed by means of a cover glass.

Measurement Parameters:
Scan range: 2-40 degrees 2-theta;
Scan mode: continuous;
Step size: 0.05 degrees;
Time per step: 0.5 s;
Sample spin: 30 rpm;
Sample holder: PMMA specimen holder ring.

EXAMPLES

The present invention will now be exemplified by the following non-limiting examples.

Example 1a: Preparation of Compound of Formula-III from Compound of Formula-IV

The compound of formula-IV (5 g) was dissolved in dichloromethane (80 ml) and cooled to −5° C. to −10° C. and a solution was formed. To this solution 2-bromo pyridine (4 g) was added and followed by slow addition of triflic anhydride (3.9 g) while maintaining the temperature below −5° C. The temperature of the reaction mixture was maintained below −5° C. and the reaction mixture was stirred for 30 min. Then, a mixture of (2-methyl-1,3-dioxolan-2-yl) methanamine (2.93 g) in dichloromethane (20 ml) was added slowly to the reaction mixture and the combined mixture was stirred for about 30 minutes. After that, water (50 ml) was added to the reaction mixture and the layer was separated. The solvent was removed to get a residue. After removal of solvent 5.1 g (yield 80%, HPLC purity 93%) product as oil was obtained.

Example 1-b: Preparation of Compound of methyl-3-((S)-2-(2,2-dimethoxypropylamino)-7-bromo-5-(pyridin-2-yl)-3H-benzo[e][1,4]diazepin-3-yl)propanoate) (Formula-III-13) from Compound of Formula-IV (3 S)-(7-BroMo-2-oxo-5-pyridin-2-yl-2,3-dihydro-1H-benzo[e][1,4]diazepin-3-yl)-propionic acid Methyl ester (Compound of formula IV, S enantiomer, 25.0 gr) and dichloromethane ("MDC", 375 ml) were charged into a clean, dry 4 neck RBF. The reaction mixture was stirred for 5-10 minutes at temperature of 20-25° C. and a clear solution was obtained. 2-bromo pyridine (29.46 gr) was added to the solution and the obtained reaction mixture was stirred for 5-10 minutes. The obtained reaction mass was cooled down to a temperature of −15° to −20° C. Then, Triflic anhydride (26.32 gr) was slowly added, over a period of 30-45 minutes to the cooled reaction mass, at the same temperature of −15° to −20° C. After the addition was completed, the obtained reaction mixture was stirred for 30-45 minutes, at the same temperature of −15° to −20° C. The reaction progress was monitored by HPLC (monitor intermediate (S)-3-(2-(methoxycarbonyl)ethyl)-7-bromo-5-(pyridin-2-yl)-3H-benzo[e][1,4]diazepin-2-yl trifluoromethanesulfonate formation). Afterwards, 1-amino-2,2-dimethoxypropane (14.81 gr) in dichloromethane (2 vol, 50 mL) solution was slowly added over a period of about 30 minutes to the reaction mixture at temperature of −15° to −20° C. After complete addition, Triethylamine (31.44 gr) was slowly added over a period of about 30 minutes at the same temperature of −15° to −20° C., and the obtained mixture was stirred at temperature of −15° to −20° C. for 60-120 minutes. The reaction progress was monitored by HPLC. After the reaction was completed, ammonium chloride solution (20%, 125 ml) was added, and the temperature was raised to 15-20° C.; the obtained mixture was stirred for 30 minutes. The organic layer was separated, washed with DM water (125 ml) and re-separated. The organic layer was then concentrated to volume of 1-1.5 vol, at a temperature below 45° C. Toluene (50 ml) was added to the reaction mass, and then stripped out 1 vol under vacuum at a temperature below 60° C. Then, Toluene (50 ml) was added and the obtained mixture was heated to temperature of 60-65° C., and was stirred at this temperature for 30-45 minutes. Heating was discontinued and the reaction mass was slowly cooled to temperature of 0-10° C., and was stirred for 3-4 hours-crystallization occurred. The obtained suspension was stirred at temperature of 0-10° C. for 30-45 minutes. The obtained solid was filtered and washed twice with pre-cooled (temperature of about 5-10° C.) toluene (12.5 ml×2 times), and suck-dried for 20-30 minutes. The wet solid was further dried under vacuum at temperature of 40-45° C. for 6-8 hours. Yield (dry): 26.5 gm (85%).

Example 2: Isolation of Compound of Formula-III as HCl Salt

The product obtained in example-1 was dissolved in ethyl acetate (50 ml) and Ethyl acetate:HCl (4 ml) was added drop wise to the reaction mixture at a temperature of about 10° C. to 15° C. The reaction mixture was stirred for 30 minutes and then precipitation occurred. The precipitate was filtered out and washed with Ethyl acetate (10 ml). Finally dried product was obtained (5.2 g).

Example 3: Isolation of Compound of Formula-III as Benzene Sulfonic Salt

The product obtained in example-1 was dissolved in ethyl acetate (40 ml) and then a mixture of Benzene sulfonic acid (1.6 g) and ethyl acetate (10 ml) at 10° C. to 15° C. was added drop wise to the reaction mixture. The reaction mixture was stirred for 30 minutes, and then precipitation occurred. The precipitate was filtered out and washed with Ethyl acetate (10 ml). Finally dried product was obtained (5.4 g).

Example 4: Preparation of Compound of Formula-I from HCl Salt of Compound of Formula-III HCl salt of compound of formula-III (5 g) was dissolved in Methanolic HCl (20 ml) and the temperature was maintained 25° C. to 30° C. The obtained reaction mixture was stirred for 10 to 12 hours. After that, the solvent was removed to get a residue. The obtained residue was neutralized with Triethyl amine (8 g). Ethyl acetate (50 ml) was added and the layers separated. The organic layer was washed with water (25 ml). Ethyl acetate was distilled and a residue was obtained (4.4 g).

Example 5a: Preparation of Compound of Formula-I from Compound of Formula-III

The compound of formula-III (5.1 g) was dissolved in Methanolic HCl (20.4 ml) and temperature was maintained 25° C. to 30° C. The obtained reaction mixture was stirred for 10 to 12 hours. After that, the solvent was removed to get a residue. The obtained residue was neutralized with Triethyl amine (8 g). Ethyl acetate (50 ml) was added and the layers separated. The organic layer was washed with water (25 ml). Ethyl acetate was distilled and a residue was obtained (4.4 g).

Example 5b: Preparation of Compound of Formula-I from Compound of Formula III-13

The compound of formula III-13 (methyl 3-((S)-2-(2,2-dimethoxypropylamino)-7-bromo-5-(pyridin-2-yl)-3H-benzo[e][1,4]diazepin-3-yl)propanoate) (20.0 g) was dissolved in methanol (40 mL) under stirring for 4-10 minutes at 20-25° C. The reaction mixture was cooled to 15° C. and slowly charged 10% Methanolic HCl solution (87.0 g) then slowly raised the temperature up to 20-25° C. and maintained under stirring for 3-6 hours to complete the reaction. The reaction mass was cooled to 5-10° C. and quenched with aqueous sodium carbonated solution (13.0 g Sodium carbonate in 200 mL water) and added dichloromethane (100 mL) and stir for 15-20 minutes. The organic layer was extracted in dichloromethane (50 mL×2) and washed with water (50 mL). The organic layer was charged with activated carbon (2.0 g) and maintained for 30 minutes at 35-40° C. Reaction mass was filtered through hyflo bed and washed with hot dichloromethane (20 mL). The clear solution was distilled off under vacuum below 45° C. up to 40-60 ml reaction mass remains inside. Then methyl acetate (60 mL) was added and stripped out 20-30 mL solvent atmospherically below 65° C. The solution obtained was Remimazolam base (Yield: 14.8-16.6 g) with above 95% HPLC purity.

Example 6: Preparation of Compound of Formula-I Besylate Salt

The residue obtained in example-4 (4.4 g) was dissolved in ethyl acetate (40 ml) and a mixture of Benzene sulfonic acid (1.5 g) and methanol (4 ml) at 10° C. to 15° C. was added drop wise to the reaction mixture. The reaction mixture was stirred for about 3 to 4 hours then precipitation occurred. The precipitate was filtered out and washed with Ethyl acetate (10 ml). Finally dried product was obtained (4.7 g).

Example 7: Preparation of Compound of Formula-II from Compound of Formula-IV

The compound of formula-IV (2 g) was dissolved in dichloromethane (20 ml) and the obtained solution was cooled to −5° C. to −10° C. 2-bromo pyridine (1.58 g) was added to the reaction mixture. Triflic anhydride (1.6 g) was slowly added to the reaction mixture at a temperature of below −5° C. The temperature of reaction mixture was maintained below −5° C. for 30 min. Then, 1-Aminopropan-2-ol (0.75 g) and dichloromethane (4 ml) were slowly added mixture while the temperature was maintained below −5° C. for about 30 min. Water was added to the reaction mixture and the layers were separated. The organic layer was distilled off to obtain a residue. The residue was purified with silica column chromatography in Hexane and Ethyl acetate solvents. Product (2.2 g, Yield=96%; HPLC purity=93%) was isolated.

Example 8: Preparation of Compound of Formula-II Hydrochloride Salt from Compound of Formula-IV The compound of formula-IV (2 g) was dissolved in dichloromethane (20 ml) and the obtained solution was cooled to −5° C. to −10° C. 2-Bromo pyridine (1.58 g) was added to the reaction mixture. Triflic anhydride (1.6 g) was slowly added to the reaction mixture at a temperature below −5° C. The temperature of reaction mixture was maintained below −5° C. for 30 min. Then, 1-Aminopropan-2-ol (0.75 g) and dichloromethane (4 ml) were slowly added to the mixture and temperature was maintained below −5° C. for about 30 min. Water was added to the reaction mixture and the layers separated. The organic layer was distilled off to obtain a residue. The obtained residue was dissolved in ethyl acetate (40 ml) and slowly added methanolic hydrochloride (about 23 ml). The precipitated product was filtered and dried to obtain 2.1 g (85%) as solid product.

Example 9: Preparation of Compound of Formula-V-A from Compound of Formula-VI

The compound of formula-VI (9.4 g) was dissolved in 100 ml toluene at room temperature the obtained solution was cooled to a temperature below 20° C. To this solution, triflic acid (6.4 ml) was added while maintaining the reaction mixture at a temperature of 15 to 10° C. The mixture was stirred for 24 hours at a temperature of 45° C. to 50° C. The solvent was distilled out from the reaction mixture and product was isolated as solid (9 g, yield 90%).

Example 10—Preparation of Remimazolam Hydrochloride Form 1

Remimazolam (4.0 g) was dissolved in ethyl acetate (36.0 mL), and then slowly added into 3.5 mL ethyl acetate-hydrochloric acid (9.0%) solution under stirring in 10 minutes at 20-30° C. which leads to immediate crystallization. The slurry mass was stirred for 60-90 minutes at 20-30° C. Filtered, washed with ethyl acetate (6.0 mL) and was kept under suction in inert atmosphere for 5-10 minutes at 25±5° C. Then, wet cake was dried at 40±5° C. under vacuum for 3 hours. The solid obtained was Remimazolam hydrochloride salt (Yield: 2.5 g).

The XRPD diffractogram of the obtained product is shown in FIG. 9.

Example 11—Preparation of Remimazolam Dihydrobromide Form 1

Remimazolam (5.0 g) was dissolved in acetone (75.0 mL) and then slowly added 2.0 mL HBr solution (48%) under stirring at 20-25° C. and maintained for 1 hr. The reaction mixture was filtered, washed with acetone (20.0 mL) and suck dried under nitrogen atmosphere. Wet cake was dried under vacuum at 40±5° C. for 3 hours. The solid obtained was Remimazolam dihydromide salt (Yield: 5.3 g).

The XRPD diffractogram of the obtained solid is shown in FIG. 10.

Example 12—Preparation of Remimazolam Fumarate Form 1

Remimazolam (5.0 g) was dissolved in ethanol (25 mL) at 20-30° C. and then added fumaric acid (1.3 g) under stirring and maintained for 10-15 minutes. The clear solution was cooled down to 0-5° C. in 20-30 minutes and crystallization was observed after 2 hours. The reaction mixture was maintained for 8-10 hours under stirring at 0-5° C., filtered and suck dried under nitrogen atmosphere for 5-10 minutes. Wet cake was dried under vacuum at 40±5° C. for 4 hours. The solid obtained was Remimazolam mono-fumarate salt (Yield: 1.5 g).

The XRPD diffractogram of the obtained solid is shown in FIG. 11.

Example 13—Preparation of Remimazolam Oxalate Form 1

Remimazolam (4.0 g) was dissolved in acetone (80 mL) and then added oxalic acid (0.819 g) under stirring at 20-30° C. and maintained for 10 minutes. The reaction mixture was filtered and the clear solution was cooled down to 0-10° C. and maintained for 60-90 minutes. The crystallization was observed at 0-5° C. after 30 minutes. The solid obtained was filtered, washed with acetone (20 mL), suck dried under nitrogen atmosphere. Wet cake was dried at 40±5° C. under vacuum for 3 h. The solid obtained was Remimazolam oxalate salt. (Yield: 3.1 g).

The XRPD diffractogram of the obtained solid is shown in FIG. 12.

Example 14—Preparation of Remimazolam Sulphate Form 1

Remimazolam (4.0 g) was dissolved in acetone (80.0 mL) and then slowly added conc. sulphuric acid (0.910 g) under stirring at 20-30° C. which leads to immediate crystallization in 10 minutes. The slurry mass was maintained at 20-30° C. under stirring for 60-90 minutes. Filtered, washed with acetone (20.0 mL) and suck dried under nitrogen atmosphere. Wet cake was dried under vacuum at 40±5° C. for 3 hours. The solid obtained was Remimazolam mono-sulphate salt (Yield: 4.4 g).

The XRPD diffractogram of the obtained solid is shown in FIG. 13.

Example 15—Preparation of Remimazolam Methane Sulfonate Form 1

Remimazolam (3.0 g) was dissolved in acetone (60.0 mL) and then slowly added methane sulfonic acid (0.656 g) under stirring at 20-30° C. in 10 minutes which leads to immediate crystallization. The slurry mass was maintained at 20-30° C. under stirring for 60-90 minutes. Filtered, washed with acetone (15.0 mL) and suck dried under nitrogen atmosphere. Wet cake dried at 40±5° C. under vacuum for 4 hours. The solid obtained was Remimazolam methane sulfonate salt (Yield: 3.1 g).

The XRPD diffractogram of the obtained solid is shown in FIG. 14.

Example 16—Preparation of Remimazolam Camphor Sulfonate Form 1

Remimazolam (3.0 g) was dissolved in acetone (45 ml) and then added R-(−)-Camphor sulfonic acid (1.6 g) under stirring at 20-30° C. which leads to immediate crystallization. The slurry mass was maintained at 20-30° C. under stirring or 60-90 minutes. Filtered, washed with acetone (20 ml) and suck dried under nitrogen atmosphere. Wet cake was dried under vacuum at 40±5° C. for 4 h. The solid obtained was Remimazolam mono-camphor sulfonate salt (Yield: 3.5 g).

The XRPD diffractogram of the obtained solid is shown in FIG. 15.

Example 17—Preparation of Remimazolam Dibesylate Form 1

Remimazolam besylate Form 1 (1.0 g) was taken in a 50 mL round bottom flask and dissolved in ethanol (14 mL) at 40-45° C. The reaction mixture was filtered to remove any undissolved particulate and a clear solution was obtained. Subsequently, ethanolic solution of benzenesulfonic acid (0.34 g of benzenesulfonic acid in 7.0 mL ethanol) was added under stirring and maintained at 40-45° C. for 1 hour. The clear solution was slowly cooled down to 20-25° C. for 4 hours. The reaction mixture was further cooled to 0-10° C. in 1 hour and maintained under stirring for 16-18 hours, then filtered and suck dried for 5-10 minutes. The solid obtained was Remimazolam dibesylate salt (Yield: 0.65 g). Remimazolam dibesylate salt Form 1 is hydrate.

The XRPD diffractogram of the obtained solid is shown in FIG. 16.

Example 18—Preparation of Remimazolam Camphor Sulfonate Form 2

Remimazolam (20.0 g) was dissolved in acetone (300 mL) in 500 ml round bottom flask then added R-(-)-Camphor sulfonic acid (10.5 g) at 20° C.-25° C. The obtained slurry mass were maintained under stirring for 2 hours at 20-25° hrs at 200-300 rpm. The reaction mixture was filtered, washed twice with acetone (60 mL) and suck dried the material under vacuum by blanketing with nitrogen atmosphere for 15 min at 20-25° C. The wet cake was dried under vacuum at 45° C. for 8 hr. The solid obtained was Remimazolam mono-camphor sulfonate salt (Yield: 18 g).

The XRPD diffractogram of the obtained solid is shown in FIG. 17.

Example 19—Preparation of Remimazolam HBR Form 1

Remimazolam (20.0 g) was dissolved in acetone (300 mL) in 500 ml round bottom flask and the obtained solution were stirred at 200-300 rpm for 5 to 10 minutes at 20-25° C. and then aqueous solution of HBr (48%) was added in 20 min under stirring at 20-25° C. and maintained for 2 hours at 20-25° C. The reaction mixture was filtered, washed twice with acetone (40 mL) and suck dried under vacuum by blanketing with nitrogen atmosphere for 15 minutes at 20-25° C. The wet cake was dried under vacuum at 45° C. for 8 hours. The solid obtained was Remimazolam mono hydrobromide salt (Yield: 17.8 g).

The XRPD diffractogram of the obtained solid is shown in FIG. 18.

Example 20—Preparation of Remimazolam Methane Sulfonate Form 2

Remimazolam (20.0 g) was dissolved in acetone (400 mL) in 500 ml round bottom flask then added methane sulfonic acid (4.3 g) and the obtained slurry mass were maintained under stirring at 20-25° C. for 2 hours at 200-300 rpm. The reaction mixture was filtered, washed twice with acetone (50 mL) and suck dried under vacuum by blanketing with nitrogen atmosphere for 15 minutes at 20-25° C. Wet cake was dried under vacuum at 45° C. for 8 hr. The solid obtained was Remimazolam methane sulfonic acid salt (Yield: 18.5 g).

The XRPD diffractogram of the obtained solid is shown in FIG. 19.

The invention claimed is:

1. A compound of Formula III-A, its salts, solvates, hydrates or isomers thereof:

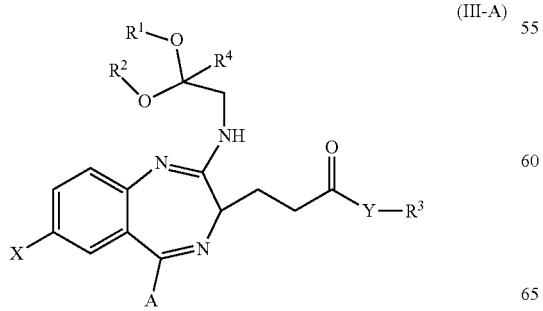

(III-A)

wherein, $R^1$ and $R^2$ are independently alkyl or they are connected to form a cyclic ring;

$R^3$ and $R^4$ are independently H, alkyl, acyl, vinyl or allyl;

X is any halogen;

Y is O, S or N; or Y is $NR^5$ wherein $R^5$ is H, alkyl, acyl, vinyl or allyl; and A is alkyl or aliphatic, aromatic or heterocyclic ring.

2. The compound of formula III-A according to claim 1, wherein alkyl includes $C_1$-$C_{12}$ straight chain or branched alkyl.

3. The compound of formula III-A according to claim 1 wherein cyclic ring includes $C_1$-$C_{12}$.

4. The compound of formula III-A according to claim 1, wherein it is physically separated from the reaction mixture in which it is formed.

5. The compound of formula III-A according to claim 1, wherein it is crystalline.

6. A process for preparing the compound of formula III-A according to claim 1, comprising preparing the compound of formula IV-A:

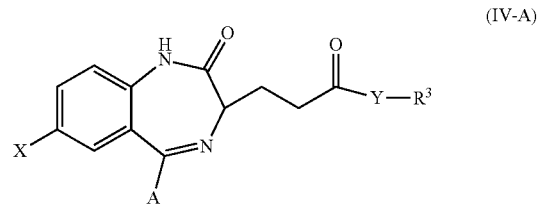

(IV-A)

wherein X, A and $R^3$ are as defined above, and converting it to the compound of Formula-III-A.

7. The compound of formula III-A according to claim 1, wherein $R^1$ and $R^2$ are connected to form a cyclic ring and the compound is a compound of Formula III, its salts, solvates, hydrates or isomers thereof:

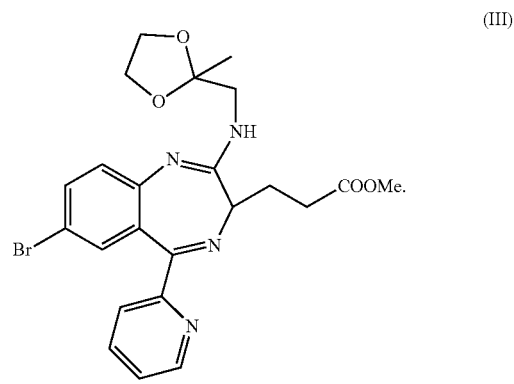 [SMILES: COC(=O)CCC1N=C(c2ccccn2)c2cc(Br)ccc2N=C1NCC1(C)OCCO1]

(III)

8. The compound of formula III according to claim 7, wherein it is physically separated from the reaction mixture in which it is formed.

9. The compound of formula III according to claim 7, wherein it is crystalline.

10. The compound of formula III according to claim 7, wherein it is in S configuration:

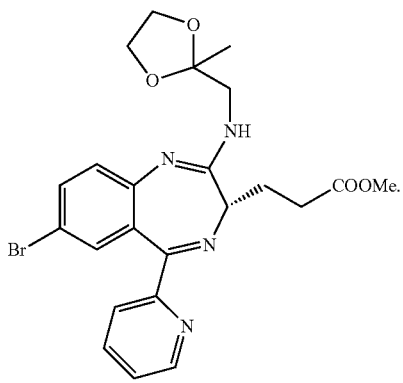
(III-S)

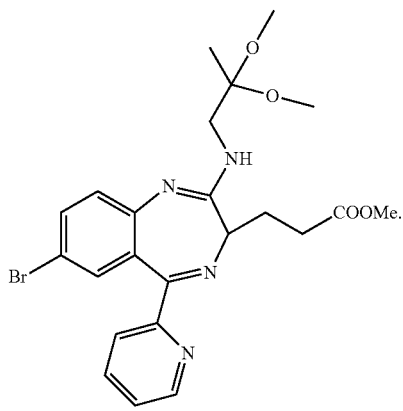
(III-13)

11. The compound of formula III according to claim 10, characterized by
   a. mass spectra as shown in FIG. 1;
   b. $^1$-NMR as shown in FIG. 2; and
   combinations thereof.

12. The compound of formula III according to claim 11, wherein the crystalline compound is characterized by data selected from one or more of the following
   a. $^{13}$C-NMR Spectra as shown in FIG. 3;
   b. IR Spectra as shown in FIG. 4; and
   c. combinations of these data.

13. A process for preparing the compound of formula III according to claim 7, comprising reacting a compound of formula IV:

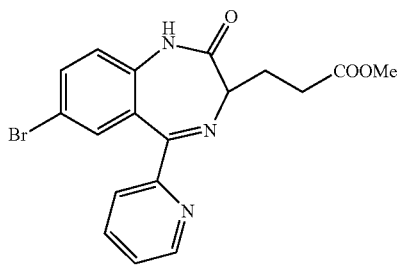
(IV)

and an amino ketal compound in presence of a carbonyl activating group to obtain the compound of formula III.

14. The compound of formula III-A according to claim 1, wherein R$^1$ and R$^2$ are each methyl and the compound is compound of Formula III-13, its salts, solvates, hydrates or isomers thereof:

15. The compound of formula III-13 according to claim 14, wherein it is physically separated from the reaction mixture in which it is formed.

16. The compound of formula III-13 according to claim 14, wherein it is crystalline.

17. The compound of formula III-13 according to claim 14, wherein it is in S configuration:

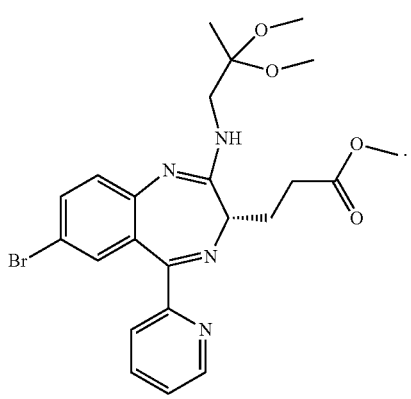
(III-13S)

18. The compound of formula III-13 according to claim 17, characterized by
   a. mass spectra as shown in FIG. 5;
   b. $^1$H-NMR as shown in FIG. 6; and
   c. combinations thereof.

19. The compound of formula III-13 according to claim 18, wherein the crystalline compound is characterized by data selected from one or more of the following
   a. $^{13}$C-NMR Spectra as shown in FIG. 7;
   b. IR Spectra as shown in FIG. 8; and
   c. combinations of these data.

20. A process for preparing the compound of formula III-13 according to claim 14, comprising reacting a compound of formula IV and an amino ketal compound in presence of a carbonyl activating group to obtain the compound of formula III-13.

* * * * *